US009833510B2

(12) United States Patent
Lee et al.

(10) Patent No.: US 9,833,510 B2
(45) Date of Patent: *Dec. 5, 2017

(54) MODIFIED RELEASE SOLID OR SEMI-SOLID DOSAGE FORMS

(75) Inventors: Der-Yang Lee, Flemington, NJ (US); Robert Shen, North Wales, PA (US); Jen-Chi Chen, Morrisville, PA (US); Vincent Chen, Dayton, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 1195 days.

This patent is subject to a terminal disclaimer.

(21) Appl. No.: 11/761,698

(22) Filed: Jun. 12, 2007

(65) Prior Publication Data

US 2008/0311201 A1 Dec. 18, 2008

(51) Int. Cl.
| A61K 9/24 | (2006.01) |
| A61K 45/06 | (2006.01) |
| A61K 9/20 | (2006.01) |
| A61K 9/48 | (2006.01) |
| A61K 31/137 | (2006.01) |
| A61K 31/192 | (2006.01) |
| A61K 9/50 | (2006.01) |

(52) U.S. Cl.
CPC ............ *A61K 45/06* (2013.01); *A61K 9/2081* (2013.01); *A61K 9/4808* (2013.01); *A61K 31/137* (2013.01); *A61K 31/192* (2013.01); *A61K 9/5073* (2013.01); *A61K 9/5084* (2013.01)

(58) Field of Classification Search
None
See application file for complete search history.

(56) References Cited

U.S. PATENT DOCUMENTS

| 2,793,979 | A | * | 5/1957 | Svedres ........................ 424/470 |
| 3,185,626 | A | | 5/1965 | Baker |
| 3,485,719 | A | | 12/1969 | Rogovin |
| 4,221,778 | A | | 9/1980 | Raghunathan |
| 4,279,926 | A | | 7/1981 | Bruzzese et al. |
| 4,543,370 | A | | 9/1985 | Porter et al. |
| 4,643,894 | A | | 2/1987 | Porter et al. |
| 4,683,256 | A | | 7/1987 | Porter et al. |
| 4,725,441 | A | | 2/1988 | Porter et al. |
| 4,749,722 | A | * | 6/1988 | Sunshine ............... A61K 31/19 514/567 |
| 4,752,580 | A | | 6/1988 | Downs |
| 4,788,220 | A | | 11/1988 | Mody et al. |
| 4,802,924 | A | | 2/1989 | Woznicki et al. |
| 4,828,841 | A | | 5/1989 | Porter et al. |
| 4,847,077 | A | | 7/1989 | Raghunathan |
| 4,863,741 | A | * | 9/1989 | Becker ........................ 424/465 |
| 4,873,231 | A | | 10/1989 | Smith |
| 4,906,478 | A | | 3/1990 | Valentine et al. |
| 4,975,465 | A | | 12/1990 | Motola et al. |
| 5,085,865 | A | * | 2/1992 | Nayak ..................... A61K 9/209 424/465 |
| 5,183,829 | A | | 2/1993 | Caldwell |
| 5,275,822 | A | | 1/1994 | Valentine et al. |
| 5,358,502 | A | * | 10/1994 | Herbig ................. A61K 9/0004 424/453 |
| 5,374,659 | A | | 12/1994 | Gowan, Jr. |
| 5,409,907 | A | | 4/1995 | Blase et al. |
| 5,424,075 | A | | 6/1995 | Daher et al. |
| 5,445,829 | A | * | 8/1995 | Paradissis ............ A61K 9/5078 424/457 |
| 5,510,385 | A | | 4/1996 | Stroppolo et al. |
| 5,595,758 | A | * | 1/1997 | Adusumilli .......... A61K 9/4808 424/451 |
| 5,621,005 | A | | 4/1997 | Gowan, Jr. |
| 5,630,871 | A | | 5/1997 | Jordan |
| 5,658,589 | A | | 8/1997 | Parekh et al. |
| 5,980,882 | A | | 11/1999 | Eichman |
| 6,001,392 | A | * | 12/1999 | Wen et al. ..................... 424/486 |
| 6,103,260 | A | | 8/2000 | Luber et al. |
| 6,149,943 | A | | 11/2000 | McTeigue et al. |
| 6,211,246 | B1 | | 4/2001 | Gelotte et al. |
| 6,228,398 | B1 | | 5/2001 | Devane et al. |
| 6,254,886 | B1 | | 7/2001 | Fusca et al. |

(Continued)

FOREIGN PATENT DOCUMENTS

CA 2568443 12/2005
EP 0 225 615 A 6/1987
(Continued)

OTHER PUBLICATIONS

Haslam, John L. et al.; "Tableting of Controlled release multiparticulates, the effect of millisphere size and protective overcoating," 1998, Elsevier, International Journal of Pharmaceutics, vol. 173, pp. 233-242.*

Dashevsky, A. et al.; "pH-independent release of a basic drug from pellets coated with the extended release polymer dispersion Kollicoat® SR 30 D and the enteric polymer dispersion Kollicoat® MAE 30 DP," 2004, Elsevier, European Journal of Pharmaceutics and Biopharmaceutics, vol. 58, pp. 45-49.*

Leopold, Claudia S.; "A Practical Approach in the Design of Colon-specific Drug Delivery Systems," 2001, Wiley-VCH Verlag GmbH; Drug Targeting Organ-Specific Strategies, Chapter 6, pp. 157-170.*

Eccles, Ronald; "Substitution of phenylephrine for pseudoephedrine as a nasal decongestant. An illogical way to control methamphetamine abuse," 2006; Blackwell Publishing; British Journal of Clinical Pharmacology, vol. 63, No. 1, pp. 10-14.*

(Continued)

*Primary Examiner* — Devang K Thakor
*Assistant Examiner* — Ivan A Greene
(74) *Attorney, Agent, or Firm* — Laura A. Donnelly

(57) ABSTRACT

A solid or semi-solid pharmaceutical dosage form comprising non-steroidal-anti-inflammatory drugs, in particular propionic acid derivatives such as ibuprofen, along with a second active ingredient having a shorter therapeutically effective plasma concentration duration, such as phenylephrine, and methods of administering the same are provided. This method provides improved therapeutic effect, in particular pain relief along with decongestant relief, over extended time periods.

17 Claims, No Drawings

(56) References Cited

U.S. PATENT DOCUMENTS

| | | | |
|---|---|---|---|
| 6,274,162 B1 | 8/2001 | Steffenino et al. | |
| 6,365,184 B1* | 4/2002 | Depui et al. | 424/469 |
| 6,699,502 B1* | 3/2004 | Fanara et al. | 424/484 |
| 6,814,978 B2 | 11/2004 | Bunick et al. | |
| 6,893,662 B2* | 5/2005 | Dittmar et al. | 424/472 |
| 6,902,742 B2* | 6/2005 | Devane et al. | 424/472 |
| 7,101,573 B2 | 9/2006 | Szymczak et al. | |
| 7,157,100 B2 | 1/2007 | Doshi et al. | |
| 2003/0099711 A1* | 5/2003 | Meadows et al. | 424/474 |
| 2004/0224020 A1* | 11/2004 | Schoenhard | 424/471 |
| 2005/0036977 A1 | 2/2005 | Gole et al. | |
| 2005/0069580 A1* | 3/2005 | Hirsh et al. | 424/452 |
| 2005/0191349 A1* | 9/2005 | Boehm et al. | 424/464 |
| 2005/0249802 A1* | 11/2005 | Khanolkar et al. | 424/456 |
| 2006/0008527 A1* | 1/2006 | Lagoviyer et al. | 424/473 |
| 2006/0057205 A1* | 3/2006 | Srinivasan et al. | 424/472 |
| 2007/0122482 A1 | 5/2007 | Holm et al. | |
| 2008/0020055 A1* | 1/2008 | Monteith et al. | 424/497 |
| 2008/0118571 A1 | 5/2008 | Lee et al. | |
| 2015/0342882 A1 | 12/2015 | Lee et al. | |

FOREIGN PATENT DOCUMENTS

| | | |
|---|---|---|
| EP | 0 564 154 A | 10/1993 |
| WO | WO 02/062299 A | 8/2002 |
| WO | WO 2006/017159 A | 2/2006 |
| WO | WO 06/022996 | 3/2006 |
| WO | WO 2006022996 A2 * | 3/2006 |
| WO | WO 08/064192 | 5/2008 |

OTHER PUBLICATIONS

Bodmeier, Roland; "Tableting of coated pellets," 1997, Elsevier, European Journal of Pharmaceutics and Biopharmaceutics, vol. 43, pp. 1-8.*

European Pharmacopeia, Monograph for "Phenylepherine" and "Phenylephrine Hydrochloride," 2005, Counsil of Europe, 5th ed. pp. 2231-2232.*

Drugs.com entry for "ibuprofen" retrieved from <www.drugs.com> on Jan. 19, 2011, pp. 1-5.*

Drugs.com entry for "pseudoephedrine" retrieved from <www.drugs.com> on Jan. 19, 2011, pp. 1-4.*

Drugs.com entry for "phenylephrine" retrieved from <www.drugs.com> on Jan. 19, 2011, pp. 1-6.*

Drugs.com entry for "ibuprofen and pseudoephedrine" retrieved from <www.drugs.com> on Jan. 19, 2011, pp. 1-4.*

Drugs.com entry for "Dristan Sinus" retrieved from <www.drugs.com> on Jan. 19, 2011, pp. 1-4.*

Gavrilin, M. V. et al.; "Study of the interaction of ibuprofen with various polymers," 1999, Kluwer Academic/Plenum Publishers; Pharmaceutical Chemistry Journal, vol. 33, No. 11, pp. 604-606.*

Sweetman, Sean C.; "Martindale: The complete drug reference," $33^{rd}$ ed. Pharmaceutical Press; 2002; pp. 1-90 and 1082-1102.*

Ansel, Howard C. et al.; "Pharmaceutical Dosage Forms and Drug Delivery Systems," $7^{th}$ ed. 1999, Lippincott, Williams & Wilkins, pp. 1-163 and 179-243.*

De Brabander, C. et al.; "Characterization of Ibuprofen as a Non-traditional Plasticizer of Ethyl Cellulose", 2002, Wiley-Liss Inc., Journal of Pharmaceutical Sciences, vol. 91, No. 7, pp. 1678-1685.*

Bodmeier, Ronald et al.; "The effect of curing on drug release and morphological properties of ethylcellulose pseudolatex-coated beads", 1994, Marcel Dekker inc., Drug Development and Industrial Pharmacy, vol. 20, No. 9, pp. 1517-1533.*

Wu, Chuanbin et al.; "Non-traditional plasticization of polymeric films", 1999, Elsevier, International Journal of Pharmaceutics, vol. 177, pp. 15-27.*

Allen, Loyd V., et al.; "Ansel's Pharmaceutical Dosage Forms and Drug Delivery Systems," 2005, Lippincott, Williams & Wilkins, 8th ed., p. 247-253 & 339.*

Allen, Loyd V., et al.; "Ansel's Pharmaceutical Dosage Forms and Drug Delivery Systems," 2005, Lippincott, Williams & Wilkins, 7th ed., p. 1-242.*

Lachman, Leon et al., "The Theory and Practice of Industrial Pharmacy", Chapter 11, pp. 293-345 (1986).

Lieberman, Herbert A. et al., Pharmaceutical Dosage Forms, Tablets, vol. 2, $2^{nd}$ Ed., pp. 213-217 and 327-329 (1990).

Lieberman, Herbert A. and Lachman, Leon, Pharmaceutical Dosage Forms, Tablets, vol. 3, Chapters 2, 3, and 4 (1982).

International Search Report PCT/US2007/085166 dated Jul. 21, 2008.

Lieberman, Herbert A. and Lachman, Leon, "Pharmaceutical Dosage Forms: Tablets", vol. 3, Chapters 2, 3, and 4, Ed. (1982).

USP 24-2000 Version, pp. 19-20 & 856 (1999).

Dubemet et al., "Ibuprofen-loaded ethylcellulose microspheres: Analysis of the matrix structure by thermal analysis," Journal of Pharmaceutical Sciences 90(11): 1029-1033 (1991).

* cited by examiner

MODIFIED RELEASE SOLID OR SEMI-SOLID DOSAGE FORMS

The present invention relates to a modified release pharmaceutical formulation suitable for solid or semi solid dosage forms for the administration of at least two active ingredients. More specifically, the dosage form releases the active ingredients at rates that provide pharmaceutically suitable plasma concentrations of all of the active ingredients contained therein over a similar period of time.

BACKGROUND OF THE INVENTION

Therapeutic agents for treating pain, inflammation, and fever include analgesics, anti-inflammatories, and antipyretics. Non-steroidal anti-inflammatory drugs (NSAID's) are one type of such therapeutic agents. They include propionic acid derivatives, acetic acid derivatives, fenamic acid derivatives, biphenylcarbodylic acid derivatives, oxicams, and cyclooxygenase-2 (COX-2) selective NSAID's.

Propionic acid derivatives include for example ibuprofen, naproxen, and ketoprofen. Ibuprofen in particular is a widely used, well known NSAID possessing analgesic and antipyretic properties. It has been commercially available as an over-the-counter drug in many forms for several years. Ibuprofen is chemically known as 2-(4-isobutylphenyl)-propionic acid.

Immediate release NSAID's are typically administered about every 4 to 6 hours. Typically, a daily dose of NSAIDs range from about 50 to about 2000 milligrams, preferably from about 100 to 1600 and most preferably from about 200 to about 1200 milligrams.

Many other active ingredients are administered more frequently due to their relatively shorter duration. For example, the therapeutically effective plasma concentration of the decongestant phenylephrine hydrochloride is about 2.5 hours±0.7 hours, and thus it is typically administered every 2 to 4 hours.

In order to administer a single product containing an NSAID and another active ingredient having a pharmaceutically suitable plasma concentration that is shorter in duration, it would be necessary to modify the release of the latter. It is well-known to reduce the rate of release of a drug or other active ingredient from a dosage form into the gastrointestinal ("g.i.") fluids of a patient, especially in order to provide prolonged action of the drug in the body.

The rate at which an orally delivered drug reaches its site of action in the body depends on a number of factors, including the rate and extent of drug absorption into the blood through the g.i. mucosa. However, before a drug can be absorbed into the blood, it must first be dissolved in the g.i. fluids. For many drugs, absorption across the g.i. membranes is relatively rapid compared to their dissolution in the g.i. fluids, which thereby renders the dissolution of the drug as the rate limiting step in drug absorption. Therefore, a formulator may effectively control the rate of drug absorption into the blood by modifying the drug's rate of dissolution.

Because the onset and duration of the therapeutic efficacy of drugs vary widely, as do their respective absorption, distribution, metabolism, and elimination, it is known to modify the release of different drugs in different ways, or to have a first drug immediately released from the dosage form, while a second drug is released in a "modified" manner, e.g., either delayed or controlled.

Well known mechanisms by which a dosage form can deliver a drug at a modified rate (e.g. sustained, prolonged, extended or retarded release) include diffusion, erosion, and osmosis. It is often practical to design dosage forms that use a combination of the above mechanisms to achieve a particularly desirable modified release profile for a particular active ingredient.

Disadvantageously, many modified release applications employ solid dosage units having a final large size and weight. The administration of such dosage units presents a problem especially to those patients with difficulty swallowing, such as children and the elderly. Therefore, it is further desirable to provide such modified release medicines either in a chewable or orally disintegratable solid form or a liquid form.

Oral liquid forms have been commonly used for many years to deliver medication with an immediate release profile. See e.g., U.S. Pat. Nos. 5,374,659; 4,788,220; 4,975,465; and 5,183,829. However, the incorporation of a modified release medication into a liquid dosage form presents significant formulation challenges. In particular, coated or chemically bonded particles are typically employed to carry the modified release portion of the drug. For example, U.S. Pat. No. 5,980,882 discloses the use of a drug-resin complex along with a chelating agent for delaying the release rate of the drug. U.S. Pat. No. 4,847,077 discloses the use of water-permeable diffusion barrier coatings on drug-resin complex particles in order to provide a prolonged continuous release of the drug.

The properties of such particles, as well as those of the matrix or suspension medium between them, must be compatible so that the particles can be maintained in a uniformly dispersed state. A particular challenge is the prevention of a premature release of drug from the particles into the matrix or suspension medium during the storage life of the dosage form prior to ingestion by a patient. Additionally, the maintenance of the desired dissolution profile as well as the desired dose uniformity of the dosage form throughout its shelf-life are additional challenges to be addressed in formulating an oral, modified release product. For example, the modified release coating of a drug particle can be compromised through several means including the physical act of compression or through chemical incompatibility with another ingredient, i.e., an active ingredient or an excipient. Disadvantageously, these issues are often encountered when formulating a product containing, for example, an immediate release ibuprofen and a modified release second active ingredient, such as phenylephrine, due to the interaction between the ibuprofen and the modified release coating agents known in the art. Chemical incompatibility of two materials in a dosage form can further be exacerbated in unfavorable conditions such as high moisture environments. These types of conditions are simulated in accelerated stability studies, which are required by regulatory agencies such as the Food and Drug Administration (FDA) for drug products.

United States Patent Application 20060057205 discloses liquid dosage forms comprising phenylephrine and at least a second drug such as an analgesic, wherein the dosage form comprises particles of a complex of both drugs with an ion-exchange resin and wherein the particles are coated with a modified release coating such as a polymethacrylate. However, we have found that uncoated propionic acid derivatives such as ibuprofen can interact with semipermeable modified release coatings, such as those containing ethyl cellulose and polymethacrylate. Deleteriously, this interaction often compromises the release rate and the intended modified release properties of the coated drug.

Copending U.S. Patent Application Ser. No. 60/860,260 discloses liquid pharmaceutical dosage forms comprising a first active ingredient, such as an NSAID, and ion exchange resin particles having a second active ingredient bound thereon to form drug-resin complex particles. The drug-resin complex particles are coated first with a semi-permeable coating layer, and then coated with a protective coating layer. This dosage form permits the second active ingredient to be released in a modified release manner such that the duration of the therapeutic effect of the second active ingredient is substantially the same as the duration of the therapeutic effect of the first active ingredient.

U.S. Pat. Nos. 6,228,398 and 7,157,100 disclose solid dosage forms in which active ingredients are released in both an immediate release and modified release manner. However, the dosage forms disclosed in these patents are not always effective for preventing an interaction between the active ingredient in the immediate release portion and the coatings on the modified release portion.

Therefore, it would be desirable to have a modified release solid or semi-solid dosage form containing a first active ingredient, such as ibuprofen, and modified release particles of another active ingredient, such as phenylephrine, which is not only palatable, but is also in a stable form that guarantees the required release profile after administration. In particular, it would further be desirable to have such a solid or semi-solid analgesic product that provided both an immediate release dose of the ibuprofen and a modified release dose of the second active ingredient to the user without interaction between the ibuprofen and the modified release coating.

SUMMARY OF THE INVENTION

The invention provides a solid or semi-solid pharmaceutical dosage form, such as a dosage form suitable for the administration of NSAIDS, and methods for its administration as claimed herein.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified. In addition, all ranges set forth herein are meant to include any combinations of values between the two endpoints, inclusively.

As used herein, "crystalline form" shall mean the non-amorphous form of the active ingredient such that it displays crystal like properties including, but not limited to, the ability to diffract visible light. Crystalline may also be used to describe an active ingredient in its pure form, i.e., e.g., without the addition of other excipients thereto.

As used herein, "cogranulated particles" shall mean particles of a crystalline active ingredient, which are co-processed with other food or pharmaceutically acceptable excipients including but not limited to fillers, disintegrants, flavors, sweeteners, acidulants, and modifying release agents. Cogranulation of particle ingredients is typically performed to modify the particle size of the active ingredient.

As used herein, the term "substantially covers" or "substantially continuous" means that the coating is generally continuous and generally covers the entire surface of the core or underlying layer, so that little to none of the active ingredient or underlying layer is exposed.

As used herein, "ATDAIRD" shall mean the average therapeutic duration of action of an effective immediate release dose" of a particular active ingredient. For example, the typical duration of action, i.e. period of therapeutic effect, of an immediate release dose of ibuprofen or ketoprofen is about 4 to about 6 hours. Accordingly, the ATDAIRD for ibuprofen or ketoprofen is 5 hours. The typical duration of action of an immediate release dose of naproxen is about 8 to about 12 hours. The ATDAIRD for naproxen, therefore is 10 hours. The typical duration of action of an immediate release dose of phenylephrine is about 2 to about 4 hours. The ATDAIRD for phenylephrine, therefore is 3 hours. The therapeutic duration of action of a particular active ingredient can readily be determined from the dosing instructions in the labeling for immediate release products containing that particular active ingredient.

As used herein, "modified release" shall apply to the altered release or dissolution of an active ingredient in a dissolution medium, such as g.i. fluids. The active ingredient or ingredients that may be released in a modified manner may be contained within, for example, dosage forms, coatings, or particles, or in any portion thereof, such as, for example, particles dispersed throughout a liquid suspending medium. Types of modified release include: 1) extended release; or 2) delayed release. In general, modified release dosage forms are formulated to make the active ingredient(s) available over an extended period of time after ingestion, which thereby allows for a reduction in dosing frequency compared to the dosing of the same active ingredient(s) in a conventional dosage form. Modified release dosage forms also permit the use of active ingredient combinations wherein the duration of one active ingredient may differ from the duration of another active ingredient.

By "extended release," it is meant that, after administration, an active ingredient is released from the dosage form in a substantially continuous, regulated manner, and the time for complete release, i.e. depletion, of the active ingredient from the dosage form is longer than that associated with an immediate release dosage form of the same. Types of extended release include controlled, sustained, prolonged, zero-order release, first-order release, pulsatile release and the like.

By "delayed release," it is meant that, after administration, there is at least one period of time when an active ingredient is not being released from the dosage form, i.e. the release of the active ingredient(s) occurs at a time other than immediately following oral administration.

As used herein, "dissolution medium" shall mean any suitable liquid environment in which the suspension dosage form of the present invention can be dissolved, such as, for example, the in vitro dissolution media used for testing of the product, or gastrointestinal fluids. Suitable in vitro dissolution media used for testing the dissolution of the active ingredient or ingredients from the suspension dosage form of the present invention include those described on page 786 of USP 23 (1995), which is incorporated by reference herein.

As used herein, "substantially coated" shall mean that less than about 20%, e.g. less than about 15%, or less than about 1.0% of the surface area of a particle is exposed, e.g. not covered, with a desired coating.

"Enteric" shall mean being able to be dissolved at a pH of greater than about 5.0 or greater than about 5.5 or greater than about 6.0 or that which is found in the intestines.

"Solid dosage forms" shall mean dosage forms which are substantially solid at room temperature and have a density of at least about 0.5 g/cc. Solid dosage forms may non exclusively include, agglomerated tablets, capsule-like medicaments, powder or granule filled capsules, powder or granule filled sachets, compressed tablets, coated tablets, chewable dosage forms, and fast-dissolving dosage forms.

"Semi-solid dosage forms" shall mean dosage forms which are highly viscous and share some of the properties of liquids, including but not limited to (1) having the ability to substantially conform to something that applies pressure to it and causes its shape to deform; and (2) lacking the ability to flow as easily as a liquid. Semi-solid dosage forms also share some of the properties of solids, including but not limited to having a higher density and a defined shape. Semi-solids may nonexclusively include gels, chewy dosage forms, pectin based chewy forms, confectionery chewy forms, moldable gelatin type of forms.

"Liquid dosage forms" may nonexclusively include suspensions or elixirs, wherein one or more of the active ingredients is dissolved, partially dissolved or in an undissolved or suspended state.

As used herein "drug-resin complex" shall mean the bound form of any of the active ingredients, including but not limited to the pharmaceutical active ingredients, and the ion exchange resin. The drug-resin complex is also referred to in the art as a "resinate."

As used herein, "immediate release" means that the dissolution characteristics of at least one active ingredient meet USP specifications for immediate release tablets containing that active ingredient. An active ingredient having an immediate release property may be dissolved in the gastrointestinal contents, with no intention of delaying or prolonging the dissolution of the active ingredient. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. See USP 24, 2000 Version, 19-20 and 856 (1999). Additionally, ibuprofen suspension may be analyzed for dissolution using pH 5.6 acetate buffer using USP apparatus 2 (paddles) at 50 rpm, where at least 80% of the ibuprofen contained in the dosage form is released therefrom within 60 minutes after dosing for an immediate release dose.

As used herein, a drug "release rate" refers to the quantity of drug released from a dosage form per unit time, e.g., milligrams of drug released per hour (mg/hr). Drug release rates are calculated under in vitro dosage form dissolution testing conditions known in the art. As used herein, a drug release rate obtained at a specified time "following administration" refers to the in vitro drug release rate obtained at the specified time following commencement of an appropriate dissolution test, e.g. those set forth in USP 24.

"Therapeutic effect," as used herein, shall mean any effect or action of an active ingredient intended to diagnose, treat, cure, mitigate, or prevent disease, or affect the structure or any function of the body.

"Semipermeable," as used herein, shall mean that water can pass through, and other molecules, including salts and the active ingredients described herein, are allowed to slowly diffuse through such a membrane when the membrane is in contact with an appropriate dissolution medium, e.g. gastro-intestinal fluids or in-vitro dissolution media.

As used herein, "water insoluble" shall mean compositions that are substantially insoluble, practically insoluble or only slightly soluble in water as defined by U.S. Pharmacopeia, $24^{th}$ edition. These compositions require at least about 100 parts of solvent per part of said composition, for complete dissolution.

"Erodible" as used herein shall mean the composition dissolves via surface erosion when in contact with an appropriate dissolution medium.

As used herein, the "protective coating" shall mean a coating that does not react with the other particles or other active ingredients in the dry vehicle, e.g. the matrix, of the dosage form or, in liquid dosage form embodiments, the liquid vehicle medium.

As used herein, the term "phenylephrine" means benzynemethanol, 3-hydroxy-α-[(methylamino)methyl], and includes, but is not limited to pharmaceutically acceptable salts, esters, isomers or derivatives thereof.

As used herein, a "particle" is a crystal, a granule, a coated crystal, a cogranulated and optionally coated active ingredient, an agglomerate, or any undissolved solid material.

One embodiment of the present invention is directed to a modified release, solid or semi-solid pharmaceutical dosage form suitable for the administration of active ingredients containing: a) a first immediate release portion, e.g., a portion containing at least one active ingredient that is immediately released from the dosage form; and b) a second modified release portion, e.g. a portion containing at least one active ingredient that is released into the bloodstream in a substantially continuous manner over a modified period of time.

In one embodiment, the active ingredient is released from the second portion in a modified release manner upon contact of the dosage form with the dissolution medium such that the modified release therapeutic effect of the second active ingredient as released from the second portion of the dosage form is substantially the same as the duration of the immediate release therapeutic effect of the first active ingredient. "Substantially the same as the duration of the immediate therapeutic effect of the first active ingredient," shall mean that the duration of therapeutic effect of the second active ingredient is the same as or within about 1 hour, i.e., e.g., within about ½ hour or within about 15 minutes or within about 10 minutes, of the duration of the first active ingredient. In another embodiment, the modified release therapeutic effect of the second active ingredient as released from the second portion of the dosage form may be, for example, at least from about 4 hours to about 6 hours, or from about 4 hours to about 8 hours, or from about 4 hours to about 12 hours, after initial administration of the dosage form.

The immediate release portion may contain one or more active ingredients that are dispersed at the molecular level, e.g. melted or dissolved, within the dosage form, or the active ingredient may be in the form of particles, which in turn may be coated or uncoated. In embodiments wherein the active ingredient is in form of particles, the particles (whether coated or uncoated) typically have an average particle size of from about 1 micron to about 2000 microns. In one embodiment, such particles are in the form of crystals having an average particle size of about 1 micron to about 300 microns. In another embodiment, the particles are in the form of granules or pellets having an average particle size of about 25 microns to about 2000 microns, for example, from about 25 microns to about 1000 microns or from about 25 microns to about 400 microns.

The modified release portion contains at least one active ingredient in a multiplicity of particles having modified release properties. In one embodiment, the particles containing active ingredient in the modified release portion may be comprised of the active ingredient in a pure, crystalline form having a particle size of about 1 micron to about 500 microns, i.e., e.g., from about 10 microns to about 200 microns, which particles are then substantially coated with a modified release composition. Alternatively, the active ingredient particle cores may be comprised of a mixture of granules comprised of one or more active ingredients with optional ingredients, such as binders, excipients and the like known in the art, and such granules are also substantially coated with a modified release composition.

In one embodiment, the active ingredient contained in the modified release portion may be substantially more soluble than the immediate release active ingredient.

In one embodiment, the particles containing active ingredient(s) may be made by first layering one or more active ingredients onto the surfaces of suitable substrate particle cores. Examples of suitable substrates include, but are not limited to, fillers, binders, disintegrants, lubricants, glidants, and the like and mixtures thereof. The substrate particle cores may have an average diameter of about 20 microns to about 1000 microns, i.e., e.g., from about 50 microns to about 200 microns. The active ingredient(s) may be dissolved or suspended in a layering solution that optionally may contain a binder, then the resulting mixture may be sprayed onto the desired substrate particle cores. The process of spraying particles is well known in the art and disclosed at, for example, U.S. Pat. No. 6,149,943. In one embodiment, the active ingredient may be layered from a solution or a suspension, which optionally contains a binder to help facilitate adhesion of the active ingredient to the substrate. The binder may be present at a level of about 0.5 percent to about 10 percent, based upon the total weight of the active layered particle core, prior to coating. Although the concentration of the active ingredient in the layering solution is not critical, one skilled in the art would readily appreciate that a sufficient amount of active ingredient should be used in order to create substantial uniformity of the desired amount of active in the final dosage form.

The layering solution is comprised of a solvent in an amount sufficient to solubilize or suspend the desired amount and type of active ingredient(s), and may include, but not be limited to water. In one embodiment, the layering solution may be comprised of, based upon the total wet weight of the layering solution, from about 0.1 percent to about 50 percent, i.e., e.g., from about 0.5 percent to about 25 percent of active ingredient(s); from about 40 percent to about 99.9 percent, i.e., e.g., from about 50 percent to about 99 percent of a solvent; and from about 0.01 percent to about 20 percent, i.e., e.g., from about 0.5 percent to about 10 percent of a binder.

The thickness of the dried, sprayed active ingredient layer on the substrate particle core is typically from about 0.5 microns to about 50 microns, e.g., from about 1 micron to about 25 microns or from about 1 micron to about 20 microns. The sprayed active ingredient layer is present in an amount, based upon the dry weight of the particle having an active ingredient layer sprayed thereon, from about 0.5 percent to about 60 percent, e.g. from about 1 percent to about 50 percent or about 10 percent to about 40 percent.

In another embodiment, the particles containing active ingredient(s) may be made by cogranulating the active ingredient(s) with suitable substrate particles via any of the granulation methods known in the art. Examples of such granulation method include, but are not limited to, high sheer wet granulation and fluid bed granulation such as rotary fluid bed granulation, the details of which are disclosed in, "The Theory and Practice of Industrial Pharmacy, $3^{rd}$ edition", Chapter 11, Lachman, Leon et. al, 1986.

Prior to cogranulation, the substrate particles may have an average diameter of about 20 microns to about 1000 microns, i.e., e.g., from about 50 microns to about 200 microns. After cogranulation, the active ingredient is present in the resulting cogranulated particles in an amount, based upon the dry weight of the cogranulated particles, from about 1 percent to about 99.5 percent, e.g. from about 10 percent to about 99 percent or about 20 percent to about 95 percent.

Suitable fillers for use in making the particle cores include, but are not limited to, water-soluble compressible carbohydrates such as, for example, sugars, which include but are not limited to dextrose, sucrose, maltose, lactose, and mixtures thereof; sugar-alcohols, which include, but are not limited to mannitol, sorbitol, lactitol, erythritol, xylitol, and mixtures thereof; starches; celluloses, which include but are not limited to microcrystalline cellulose; and mixtures thereof.

Suitable binders for making the particle cores include, but are not limited to dry binders such as, for example, polyvinyl pyrrolidone, hydroxypropylmethylcellulose, hydroxypropylcellulose, microcrystalline cellulose and the like, and mixtures thereof; wet binders such as, for example, water-soluble polymers, including hydrocolloids; polyvinyl pyrrolidone, cellulosics, and the like; and derivatives and mixtures thereof. Examples of suitable hydrocolloids include, but are not limited to acacia, alginates, agar, guar gum, locust bean, carrageenan, carboxymethylcellulose, tara, gum arabic, tragacanth, pectin, xanthan, gellan, gelatin, maltodextrin, galactomannan, pusstulan, laminarin, scleroglucan, inulin, whelan, rhamsan, zooglan, methylan, chitin, cyclodextrin, chitosan, and mixtures thereof.

Suitable disintegrants for making the particle cores include, but are not limited to sodium starch glycolate, cross-linked polyvinylpyrrolidone, crosscarmellose sodium, cross-linked carboxymethylcellulose, starches, and the like. Suitable lubricants for making the particle cores include, but are not limited to long chain fatty acids and their salts, such as magnesium stearate and stearic acid; talc; glycerides; waxes; and mixtures thereof.

Suitable glidants for making the particle cores include, but are not limited to colloidal silicon dioxide, and the like.

In accordance with the present invention, the particles containing active ingredients are substantially coated with a semipermeable coating. By "substantially coated," it is meant that about 80%, e.g., about 85% or about 99% of the particle surface is coated.

Examples of suitable semipermeable coatings include but are not limited to, polymers such as cellulose acetate, ethylcellulose, non-enteric polymethacrylates and copolymers and mixtures thereof. Exemplary non-enteric polymethacrylates include, but are not limited to, poly(ethyl acrylate, methyl methacrylate) 2:1, which is commercially available from Rohm Pharma under the tradename, "EUDRAGIT NE"; poly(methyl acrylate, methyl methacrylate, methacrylic acid) 7:3:1 which is commercially available from Rohm Pharma under the tradename "EUDRAGIT FS;" poly(ethyl acrylate, methyl methacrylate, triethylammonioethyl methacrylate chloride) 1:2:0.2, which is commercially available from Rohm Pharma under the tradename "EUDRAGIT RL"; poly(ethyl acrylate, methyl methacrylate, triethyleammonioethyl methacrylate chloride 1:2:0.1, which is commercially available from Rohm Pharma under the tradename "EUDRAGIT RS," and copolymers and mixtures thereof. Cellulose acetate, which is also known in the art under the general terms of acetyl cellulose, cellulose diacetate, and cellulose triacetate, is commercially available from the Eastman Chemical Company. Ethylcellulose, which is also known in the art as cellulose ethyl ether, is commercially available from the Dow Corporation under the tradename "ETHOCEL." In one embodiment, the semipermeable coating may be selected from cellulose acetate, ethylcellulose, and mixtures thereof.

The coated active ingredient particle cores are then substantially coated with a protective coating. By "substantially coated," it is meant that about 80%, e.g., about 85% or about 99% of the coated particle surface is then coated with a protective coating layer.

Examples of suitable protective coatings include those comprised of enteric polymers, reverse enteric polymers, lipids, waxes, elastic coatings, and copolymers and mixtures thereof. Suitable enteric polymers include, but are not limited to hydroxypropyl methylcellulose phthalate (also known as hypromellose phthalate), hydroxypropyl methylcellulose acetate succinate, cellulose acetate phthalate, polyvinylacetate phthalate, shellac, enteric polymethacrylate-based polymers, and copolymers and mixtures thereof. Examples of suitable enteric polymethacrylate-based polymers include, but are not limited to poly(methacrylic acid, methyl methacrylate) 1:2, which is commercially available from Rohm Pharma GmbH under the tradename, "EUDRAGIT S" polymers; poly(methacrylic acid, methyl methacrylate) 1:1, which is commercially available from Rohm Pharma GmbH under the tradename, "EUDRAGIT L-100, L-30D, L 12.5 and L12.5 P" polymers; and poly (methacrylic acid, ethyl acrylate) 1:1 which is commercially available from Rohm Pharma under the tradename "EUDRAGIT L30-D 55 and L-100-55," from Eastman Chemical under the tradename "Eastacryl 30D," from Colorcon Corporation under the tradename, "Acryl-EZE" and from BASF Fine Chemicals under the tradename, "Kollicoat MAE 30D." In one embodiment, the enteric polymer may be selected from non-acrylate compounds, such as hydroxypropyl methylcellulose phthalate, hydroxypropyl methylcellulose acetate succinate, cellulose acetate phthalate, polyvinylacetate phthalate, shellac and copolymers and mixtures thereof. In another embodiment the reverse-enteric polymer is poly (butyl methacrylate, (2-dimethylaminoethyyl)methacrylate, methyl methacrylate) 1:2:1, which is commercially available from Rohm Pharma under the tradename in a granular form as "Eudragit E-100" and in a micronized powder form as "Eudragit EPO."

Elastic coatings, as used herein, shall mean coatings which have an elongation at break value of at least about 70% without the addition of a plasticizer to the film, when film samples of each layer are independently tested in accordance with that described in the American Society for Testing Materials (ASTM) D882 test measurement. According to this test method, a film sample is cast and cut or stamped using an ASTM D1708 Stamp mold, then inserted into a press such as the Punch Press Model B No. 8463 as produced by the Naef Corporation. The film sample is then placed between two grippers on a texture analyzer, such as the model TA-XT2i (HR) available from Texture Technologies Corporation, which elongates the film from two ends and determines the percentage value at break. Exemplary elastic coatings suitable for use in the protective coating include, but are not limited to poly(ethyl acrylate, methyl methacrylate) 2:1, which is commercially available from Rohm Pharma under the tradename, "EUDRAGIT NE-30D," and copolymers and mixtures thereof.

The protective coating may also be provided in the form of a lipid, such as a fatty acid ester, a wax, or mixtures thereof. Examples of suitable fatty acid esters include, but are not limited to sucrose fatty acid esters; mono- di- and triglycerides; glyceryl behenate; glyceryl palmitostearate; glyceryl tristearate; glyceryl trilaurylate; glyceryl myristate; GLYCOWAX-932; lauroyl macrogol-32 glycerides; stearoyl macrogol-32 glyceride; fatty acid esters such as those having a fatty acid chain length of about $C_{10}$-$C_{40}$; and mixtures thereof.

Examples of suitable waxes include, but are not limited to carnauba wax, spermaceti wax, beeswax, candelilla wax, shellac wax, carnuba wax, beeswax, microcrystalline wax, and paraffin wax and the like, and mixtures thereof.

Optionally, the semi-permeable coating and/or the protective coating may include a plasticizer. Examples of suitable plasticizers include, but are not limited to, polyethylene glycol; propylene glycol; glycerin; sorbitol; triethyl citrate; tributyl citrate; dibutyl sebecate; vegetable oils such as castor oil, rape oil, olive oil, and sesame oil; surfactants such as polysorbates, sodium lauryl sulfates, and dioctyl-sodium sulfosuccinates; mono acetate of glycerol; diacetate of glycerol; triacetate of glycerol; natural gums; triacetin; acetyltributyl citrate; diethyloxalate; diethylmalate; diethyl fumarate; diethylmalonate; dioctylphthalate; dibutylsuccinate; glyceroltributyrate; glycerol monostearate; hydrogenated castor oil; substituted triglycerides and glycerides; and mixtures thereof.

In one embodiment, a suitable plasticizer may be used in an amount, based upon the total dry weight of the semipermeable coating, from about 0.1% to about 40%, e.g. about 1% to about 30% or from about 5% to about 20%.

In one embodiment, a suitable plasticizer may be used in an amount, based upon the total dry weight of the protective coating, from about 0.1% to about 40%, i.e., e.g., from about 1% to about 30% or from about 5% to about 20%.

In one embodiment, the weight ratio of the semipermeable coating layer to the protective coating layer in the modified release particles is about 10:90 to about 90:10, or about 20:80 to about 80:20.

In one embodiment, the modified release particles are substantially free of enteric polymers, i.e., e.g. the modified release particles contain, based upon the total weight of the modified release particles, less than about 1 percent or less than about 0.25 percent of enteric polymers.

In one embodiment the modified release active ingredient may be bound to an ion exchange resin. For example, the drug-resin complex may be treated with a solvating or impregnating agent that is added while the active ingredient and the resin are being mixed or after the active ingredient is bound to the resin. Examples of suitable impregnating agents include, but are not limited to, sorbitol, polyethylene glycol, glycerol, propylene glycol, mannitol, lactitol, lactose, methylcellulose, and mixtures thereof. The impregnating agent may be present in an amount of about 5 parts to about 50 parts per weight of the dry resin.

In one embodiment, a chelating agent may be added to the dosage form in order to stabilize the drug-resin complex by inhibiting the oxidation of the drug-resin complex. Suitable chelating agents include, but are not limited to, ethylenediaminetetraacetic acid (EDTA) and salts of EDTA including, but not limited to, edetate calcium disodium, edetate trisodium, edetate disodium, and edetate sodium. The chelating agent may be present in an amount of about 0.005 percent to about 10 percent by weight of the final dosage form.

The particle cores containing an active ingredient, which further contain a first semipermeable coating layer underneath a second protective coating later, yield a modified release composition that contains, based upon the total dry weight of such modified release composition, from about 1 percent to about 99 percent, e.g. from about 5 percent to about 80 percent of the first semipermeable coating layer; from about 5 percent to about 99 percent, e.g. from about 10 percent to about 90 percent of the second protective coating layer; and from about 5 percent to about 95 percent of the particle core, e.g. from about 20 percent to about 80 percent of the particle core.

The thickness of each of the two coating layers may vary depending upon the modified release properties desired, the active ingredient selected, and the like, but typically may range from about 0.01 microns to about 500 microns, e.g., from about 0.1 microns to about 100 microns.

The dry weight per surface area of the first coating layer on the particles is about 0.1 mg/cm$^2$ to about 10 mg/cm$^2$, i.e., e.g. from about 0.5 mg/cm$^2$ to about 5 mg/cm$^2$. The dry weight per surface area of the second coating layer on the particles is about 0.1 mg/cm$^2$ to about 10 mg/cm$^2$, e.g. about 0.5 mg/cm$^2$ to about 8 mg/cm$^2$.

The weight gain of the active ingredient particle cores after the addition of the first semipermeable coating layer thereto is, based upon the dry weight of the uncoated, active ingredient particle cores, from about 1 percent to about 200 percent, e.g., from about 20 percent to about 150 percent. The weight gain of the active ingredient particle cores after the addition of the second protective coating layer is, based upon the dry weight of the active ingredient particle cores coated with the first semipermeable coating layer, from about 25 percent to about 400 percent, e.g., from about 40 percent to about 400 percent.

The semi-permeable coating and the protective layer coating may be applied to the active ingredient particle cores via any suitable method known in the art. Suitable coating methods include high sheer granulation, fluid bed granulation, e.g. rotor granulation, fluid bed coating, wurster coating, coaccervation, spray drying, spray congealing, and the like and are described in, for example, Pharmaceutical Dosage Forms: Tablets Volume 3, edited by Herbert A. Lieberman and Leon Lachman, Chapters 2, 3, and 4 (1982).

In one embodiment, the active ingredient particle cores may be first coated with the semipermeable layer using wurster fluid bed coating, then coated using wurster fluid bed coating with an enteric protective layer. The coating materials may be sprayed onto the particles via a solution or dispersion containing solvents including but not limited to water, ethanol, methanol, acetone, hexane, cyclohexane, methylene chloride, isopropanol, and mixtures thereof. See e.g., U.S. Pat. No. 4,847,077.

In one embodiment the average diameter of the uncoated active ingredient particles is from about 20 microns to about 400 microns, or about 20 microns to about 300 microns. In one embodiment, the average diameter of the active ingredient particles coated with the first coating layer is from about 20 to about 800 microns, e.g. from about 50 microns to about 400 microns, and the average diameter of the active ingredient particles coated with both the first and second coating layers is from about 50 to about 1000 microns, e.g. from about 100 microns to about 400 microns.

The dosage form of the present invention contains one or more active agents or ingredients. Suitable active ingredients broadly include, for example, pharmaceuticals, minerals, vitamins and other nutraceuticals, oral care agents, flavorants and mixtures thereof. Suitable pharmaceuticals include analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, oral contraceptives, diuretics, expectorants, gastrointestinal agents, migraine preparations, motion sickness products, mucolytics, muscle relaxants, osteoporosis preparations, polydimethylsiloxanes, respiratory agents, sleep-aids, urinary tract agents and mixtures thereof.

Suitable flavorants include menthol, peppermint, mint flavors, fruit flavors, chocolate, vanilla, bubblegum flavors, coffee flavors, liqueur flavors and combinations and the like.

Examples of suitable gastrointestinal agents include antacids such as calcium carbonate, magnesium hydroxide, magnesium oxide, magnesium carbonate, aluminum hydroxide, sodium bicarbonate, dihydroxyaluminum sodium carbonate; stimulant laxatives, such as bisacodyl, cascara sagrada, danthron, senna, phenolphthalein, aloe, castor oil, ricinoleic acid, and dehydrocholic acid, and mixtures thereof; H2 receptor antagonists, such as famotadine, ranitidine, cimetadine, nizatidine; proton pump inhibitors such as omeprazole or lansoprazole; gastrointestinal cytoprotectives, such as sucraflate and misoprostol; gastrointestinal prokinetics, such as prucalopride, antibiotics for H. pylori, such as clarithromycin, amoxicillin, tetracycline, and metronidazole; antidiarrheals, such as diphenoxylate and loperamide; glycopyrrolate; antiemetics, such as ondansetron, analgesics, such as mesalamine.

Examples of suitable polydimethylsiloxanes, which include, but are not limited to dimethicone and simethicone, are those disclosed in U.S. Pat. Nos. 4,906,478, 5,275,822, and 6,103,260, the contents of each is expressly incorporated herein by reference. As used herein, the term "simethicone" refers to the broader class of polydimethylsiloxanes, including but not limited to simethicone and dimethicone.

In one embodiment of the invention, at least one active ingredient may be selected from bisacodyl, albuterol, famotadine, ranitidine, cimetidine, prucalopride, diphenoxylate, loperamide, lactase, mesalamine, bismuth, antacids, and pharmaceutically acceptable salts, esters, isomers, and mixtures thereof.

In another embodiment, at least one active ingredient is selected from analgesics, anti-inflammatories, and antipyretics, e.g. non-steroidal anti-inflammatory drugs (NSAIDs), including a) propionic acid derivatives, e.g. ibuprofen, naproxen, ketoprofen and the like; b) acetic acid derivatives, e.g. indomethacin, diclofenac, sulindac, tolmetin, and the like; c) fenamic acid derivatives, e.g. mefenamic acid, meclofenamic acid, flufenamic acid, and the like; d) biphenylcarbodylic acid derivatives, e.g. diflunisal, flufenisal, and the like; e) oxicams, e.g. piroxicam, sudoxicam, isoxicam, meloxicam, and the like; f) cyclooxygenase-2 (COX-2) selective NSAIDs; g) aspirin and h) pharmaceutically acceptable salts of the foregoing.

In one particular embodiment, at least one active ingredient is selected from propionic acid derivative NSAID, which are pharmaceutically acceptable analgesics/non-steroidal anti-inflammatory drugs having a free —CH(CH$_3$)COOH or —CH$_2$CH$_2$COOH or a pharmaceutically acceptable salt group, such as —CH(CH$_3$)COO—Na+ or CH$_2$CH$_2$COO—Na+, which are typically attached directly or via a carbonyl functionality to a ring system, preferably an aromatic ring system.

Examples of useful propionic acid derivatives include ibuprofen, naproxen, benoxaprofen, naproxen sodium, fenbufen, flurbiprofen, fenoprofen, fenoprofen calcium, flurbiprofen, tiaprofenic, oxaprozin, fenbuprofen, ketoprofen, indoprofen, pirprofen, carpofen, oxaprofen, pranoprofen, microprofen, tioxaprofen, suprofen, alminoprofen, tiaprofenic acid, fluprofen, bucloxic acid, and pharmaceutically acceptable salts, derivatives, and combinations thereof.

In one embodiment of the invention, the propionic acid derivative is selected from ibuprofen, ketoprofen, flubiprofen, and pharmaceutically acceptable salts and combinations thereof.

In another embodiment, the propionic acid derivative is ibuprofen, 2-(4-isobutylphenyl)propionic acid, or a pharmaceutically acceptable salt thereof, such as the arginine, lysine, or histidine salt of ibuprofen. Other pharmaceutically acceptable salts of ibuprofen are described in U.S. Pat. Nos. 4,279,926, 4,873,231, 5,424,075 and 5,510,385, the contents of which are incorporated by reference.

In another particular embodiment of the invention, at least one active ingredient may be selected from acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof.

In another particular embodiment of the invention, at least one active ingredient may be selected from pseudoephedrine, phenylephrine, phenylpropanolamine, chlorpheniramine, dextromethorphan, diphenhydramine, clofedianol, astemizole, terfenadine, fexofenadine, loratadine, desloratadine, cetirizine, mixtures thereof and pharmaceutically acceptable salts, esters, isomers, and mixtures thereof.

In a particular embodiment the active ingredient in the modified release portion is selected from phenylephrine, pseudoephedrine, dextromethorphan, diphenhydramine, chlorpheniramine and mixtures thereof.

In another particular embodiment, at least one active ingredient is an NSAID or a pharmaceutically acceptable salts thereof, and the other active ingredient in the modified release portion is phenylephrine and/or pseudoephedrine.

In another particular embodiment, the solubility of the active ingredient in the modified release portion is greater than about 5 mg/mL in water and the solubility of the active ingredient in the immediate release portion is less than about 5 mg/mL in water.

In one embodiment, a therapeutically effective amount of the active ingredient or ingredients may be present in a "unit dose volume," which can be in the form of, for example, a powder. "Therapeutically effective amount," as used herein, is an amount of active ingredient that produces the desired therapeutic response upon oral administration. One skilled in the art can readily determine the "therapeutically effective amount" of an active ingredient for a given patient by considering factors such as, for example, the particular active ingredient being administered; the bioavailability characteristics of the active ingredient; the dose regimen desired; the age and weight of the patient; and the like. As used herein, a "unit dose " may be any convenient amount (i.e. one to two tablets) for orally administering a dose of a given product to a patient.

In this embodiment, the "unit dose " is typically accompanied by dosing directions, which instruct the patient to take an amount of the active ingredient that may be a multiple of the unit dose depending on, e.g., the age or weight of the patient. Typically the unit dose will contain an amount of active ingredient that is therapeutically effective for the smallest patient., e.g. one tablet.

According to the invention, a dosage form containing NSAID may be provided to a mammal in need of treatment, in particular pain relief treatment, in a single administration that provides for the release of the active ingredient in the blood over an extended time period, e.g. over about an 4 hour or about a 6 hour period. At time zero, an initial dose of the NSAID is provided, i.e. administered, to the mammal via of the active ingredient(s) in the immediate release dose portion. The second active ingredient is then released into the blood throughout about the next four to about 6 hours from initial administration of the formulation containing the active ingredient via the active ingredient(s) in the modified release dose portion. In other words, the formulation still retains undissolved, second active ingredient after about four or about six hours from initial administration.

In practicing the present invention, the dosage form may be comprised of, based upon the total weight of the active ingredient, from about 0.01 percent to about 80 percent, i.e., e.g. about 5 percent to about 70 percent or about 1 percent to about 50 percent, of an immediate release dose particle portion of the first active ingredient; and from about 0.01 percent to about 30 percent, i.e., from about 0.01 percent to about 15 percent of a modified release dose portion of the dual coated second active ingredient. As used herein, "portion" shall mean the amount of the identified active ingredient along with any optional components, but shall not include the matrix or other dry vehicle into which the immediate release dose particles may be combined. The dosage form may be comprised, based upon the total weight of the dosage form, of from about 1 percent to about 99 percent, i.e., e.g. about 10 percent to about 90 percent, of a matrix.

The dosage form may be comprised of, based on the total weight of the dosage form, from about 0.01 percent to about 90 percent, i.e., e.g. about 1 percent to about 80 percent of the first active ingredient; and from about 0.005 percent to about 20 percent, i.e., e.g. about 0.01 percent to about 10 percent of the second active ingredient.

The immediate release dose portion and the modified release dose portion may be combined with an appropriate matrix excipients known in the art to form the dosage forms of the present invention, such as, for example: 1) a dry mixture that can be suspended extemporaneously when needed; or 2) a solid or semi solid dosage form. In one embodiment, either the immediate release active ingredient particles or the dual coated, modified release active ingredient particles are first combined with the matrix excipient, then the remaining active ingredient particles are added thereto. In embodiments in which the dosage forms are made by compression, suitable matrix excipients include fillers, binders, disintegrants, lubricants, glidants, and the like, and mixtures thereof as known in the art and set forth above. In general, the order of addition of components is not critical.

In one embodiment, the modified release portion and the immediate release portion are substantially homogeneously distributed in the matrix of the dosage form. In another embodiment, the dosage form is in the form of a multi-layer tablet, with one layer being comprised of the modified release portion and a second layer being comprised of the immediate release portion. Methods for making multi-layer dosage forms are generally known in the art, and disclosed in, for example, U.S. Pat. No. 6,254,886.

Suitable optional ingredients in the dosage form matrix can include, without limitation, antioxidants, surfactants; sugars; buffering substances such as citric acid and sodium citrate; glycine and hydrochloric acid, sodium phosphate, and potassium phosphate; preservatives and bacteriostatic agents such as esters of p-hydroxybenzoic acid; colorants; various flavorings and sweeteners commonly used in pharmaceuticals, and mixtures thereof.

Examples of suitable sweeteners include, but are not limited to any known sweetening agent such as sugars, sugar alcohols, high intensity sweeteners, and mixtures thereof. Suitable sugars include, but are not limited to sucrose, dextrose, high fructose corn syrup, and maltose. Suitable sugar alcohols include, but are not limited to sorbitol, xylitol, and mannitol. Suitable high intensity sweeteners include, but are not limited to sucralose, aspartame, saccharin, and acesulfame K.

In one embodiment, the dosage form may optionally contain antimicrobial preservatives having an activity within the desired pH range of the dosage form. Preservatives useful in such pharmaceutical suspensions include, but are not limited to, sodium benzoate, potassium sorbate, salts of edetate (also known as salts of ethylene diaminetetraacetic acid, or EDTA, such as, disodium edetate) and parabens (such as, methyl, ethyl, propyl and butyl p-hydroxybenzoic acids esters). The preservatives listed above are exemplary, but each preservative must be evaluated on an empirical basis, in each formulation, to assure the compatibility and efficacy of the preservative. Methods for evaluating the efficacy of preservatives in pharmaceutical formulations are known to those skilled in the art.

In certain optional embodiments, the dosage form of the invention may employ a surfactant for use as a wetting agent to aid in the dispersion of certain hydrophobic active agents. In certain other embodiments, the dosage form of the invention may be substantially free of surfactant. As used herein, "substantially free of surfactant" shall mean that the dosage form core contains less than about 0.1%, e.g., less than about 0.05% of a surfactant. Examples of suitable surfactants include, but are not limited to sorbitan oleate esters, such as polyoxyethylene sorbitan monooleate also known as polysorbate 80.

In an alternative embodiment in which the dosage form is made by compression and additionally confers modified release of the uncoated active ingredient contained therein, the matrix may further comprise a release-modifying compressible excipient. The amount of release-modifying compressible excipient will depend upon, for example, the type and amount of second active ingredient selected, the desired modified release, and the like, but will typically range from, based upon the total dry weight of the dosage form, from about 0.5 percent to about 80 percent, i.e., e.g., from about 1 percent to about 30 percent.

Examples of suitable release-modifying compressible excipients include, but are not limited to swellable erodible hydrophillic materials, insoluble edible materials, pH-dependent polymers, and the like, and mixtures thereof.

Suitable swellable erodible hydrophilic materials for use as release-modifying compressible excipients include, but are not limited to, water swellable cellulose derivatives, polyalkylene glycols, thermoplastic polyalkylene oxides, acrylic polymers, hydrocolloids, clays, gelling starches, and swelling cross-linked polymers, and derivatives, copolymers, and combinations thereof. Examples of suitable water swellable cellulose derivatives include, but are not limited to sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose,hydroxyphenylcellulose, hydroxyethylcellulose (HEC), hydroxypentylcellulose, hydroxypropylethylcellulose, hydroxypropylbutylcellulose, and hydroxypropylethylcellulose. Examples of suitable polyalkylene glycols include, but are not limited to polyethylene glycol. Examples of suitable thermoplastic polyalkylene oxides include, but are not limited to poly (ethylene oxide). Examples of suitable acrylic polymers include, but are not limited to potassium methacrylatedivinylbenzene copolymer, polymethylmethacrylate, high-molecular weight cross-linked acrylic acid homopolymers and copolymers commercially available from Noveon Chemicals under the tradename, "CARBOPOL," having a viscosity of greater than about 50,000 centipoise when tested using a Brookfield RVT Viscometer at 25° C., using spindle # 7, when dispersed in a basic solution. and the like. Examples of suitable hydrocolloids include, but are not limited to, alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan, and mixtures thereof. Examples of suitable clays include, but are not limited to, smectites such as bentonite, kaolin, and laponite; magnesium trisilicate; magnesium aluminum silicate; and the like, and derivatives and mixtures thereof. Examples of suitable gelling starches include, but are not limited to acid hydrolyzed starches, swelling starches such as sodium starch glycolate, and derivatives thereof. Examples of suitable swelling cross-linked polymers include cross-linked polyvinyl pyrrolidone, cross-linked agar, and cross-linked carboxymethylcellulose sodium.

Suitable insoluble edible materials include, but are not limited to, water-insoluble polymers, low-melting hydrophobic materials, and copolymers and mixtures thereof. Examples of suitable water-insoluble polymers include, but are not limited to, ethylcellulose, polyvinyl alcohols, polyvinyl acetate, polycaprolactones, cellulose acetate and its derivatives, acrylates, methacrylates, acrylic acid copolymers; and the like and derivatives, copolymers, and combinations thereof. Suitable low-melting hydrophobic materials include, but are not limited to, fats, fatty acid esters, phospholipids, and waxes. Examples of suitable fats include, but are not limited to, hydrogenated vegetable oils such as for example cocoa butter, hydrogenated palm kernel oil, hydrogenated cottonseed oil, hydrogenated sunflower oil, and hydrogenated soybean oil; and free fatty acids and their salts. Examples of suitable fatty acid esters include, but are not limited to, sucrose fatty acid esters, mono, di, and triglycerides, glyceryl behenate, glyceryl palmitostearate, glyceryl monostearate, glyceryl tristearate, glyceryl trilaurylate, glyceryl myristate, GlycoWax-932, lauroyl macrogol-32 glycerides, and stearoyl macrogol-32 glycerides. Examples of suitable phospholipids include phosphotidyl choline, phosphotidyl serene, phosphotidyl enositol, and phosphotidic acid. Examples of suitable waxes include, but are not limited to, carnauba wax, spermaceti wax, beeswax, candelilla wax, shellac wax, microcrystalline wax, and paraffin wax; fat-containing mixtures such as chocolate; and the like.

Suitable pH-dependent polymers for use as release-modifying excipients include, but are not limited to, enteric cellulose derivatives, for example hydroxypropyl methylcellulose phthalate, hydroxypropyl methylcellulose acetate succinate, cellulose acetate phthalate; natural resins such as shellac and zein; enteric acetate derivatives such as for example polyvinylacetate phthalate, cellulose acetate phthalate, acetaldehyde dimethylcellulose acetate; and enteric acrylate derivatives such as for example polymethacrylate-based polymers such as poly(methacrylic acid, methyl methacrylate) 1:2, which is commercially available from Rohm Pharma GmbH under the tradename, "EUDRAGIT S," and poly(methacrylic acid, methyl methacrylate) 1:1, which is commercially available from Rohm Pharma GmbH under the tradename, "EUDRAGIT L," and the like, and derivatives, salts, copolymers, and combinations thereof.

Tablets comprised of the particles of the present invention may be made by any means known in the art. Conventional methods for tablet production include direct compression ("dry blending"), dry granulation followed by compression, and wet granulation followed by drying and compression. Other methods include the use of compacting roller technology such as a chilsonator or drop roller, or molding, casting, or extrusion technologies. All of these methods are well known in the art, and are described in detail in, for example, Lachman, et al., "The Theory and Practice of Industrial Pharmacy," Chapter 11, ($3^{rd}$ Ed. 1986), which is incorporated by reference herein.

In one embodiment wherein the tablets are formed by the direct compression method, a blend of the dual coated active ingredient particle cores, the second active ingredient, the matrix components and any other appropriate optional ingredients are directly compacted. After blending, a pre-determined volume of particles is filled into a die cavity of a rotary tablet press, which continuously rotates as part of a "die table" from the filling position to a compaction position. The particles are compacted between an upper punch and a lower punch to an ejection position, at which the resulting tablet is pushed from the die cavity by the lower punch and guided to an ejection chute by a stationary "take-off" bar.

In embodiments wherein a chewable tablet is desired, the degree of particle compaction is controlled so that the resulting tablets are relatively soft, i.e. they have a hardness of up to about 15 kiloponds per square centimeter ($kp/cm^2$), e.g. from about 1 $kp/cm^2$ to about 10 $kp/cm^2$ or from about 2 $kp/cm^2$ to about 6 $kp/cm^2$. "Hardness" is a term used in the art to describe the diametrical breaking strength as measured by conventional pharmaceutical hardness testing equipment, such as a Schleuniger Hardness Tester. In order to compare values across different size tablets, the breaking strength is normalized for the area of the break (which may be approximated as the tablet diameter times the thickness). This normalized value, expressed in $kp/cm^2$, is sometimes referred in the art as tablet tensile strength. A general discussion of tablet hardness testing is found in Leiberman et al., 2 *Pharmaceutical Dosage Forms—Tablets*, 213-217, 327-329 ($2^{nd}$ Ed. 1990)(hereinafter "Lieberman").

In one embodiment, the dosage form is in the form of a solid or semi-solid composition and is comprised of, based upon the total weight of the solid or semi-solid composition, from greater than about 0 percent to about 30 percent, e.g. about 0.05 percent to about 20 percent, or about 0.5 percent to about 10 percent, or about 0.5 percent to about 5 percent, of the first active ingredient and from greater than about 0 percent to about 10 percent, e.g. about 0.01 percent to about 10 percent, or about 0.03 percent to about 5 percent, of the second, modified release active ingredient, which is coated with the two aforementioned coating layers.

In another embodiment wherein the immediate release active ingredient is ibuprofen, the amount of the first active ingredient in the immediate release portion of the dosage form is, based upon the total weight of the dosage form, from about 10 percent to about 80 percent, i.e., from about 20 percent to about 60 percent, and the second, modified release active ingredient is phenylephrine or pseudoephedrine, the amount of second active ingredient in the modified release portion of the dosage form is, based upon the total weight of dosage form, from about 0.005 percent to about 20 percent, i.e., e.g., from about 0.01 percent to about 10 percent.

One embodiment of the present invention is directed to a solid or semi-solid dosage form comprising, based upon the total weight of the dosage form, from about 0.1 percent to about 80 percent, i.e., e.g., from about 1 percent to about 60 percent of the first, immediate release portion; from about 0.01 percent to about 30 percent, i.e., e.g. from about 0.01 percent to about 15 percent, of the second, modified release portion; and from about 1 percent to about 99 percent, e.g., from about 10 percent to about 90 percent of a matrix.

In one embodiment, the second, modified release portion of the dosage form is comprised of, based upon the total dry weight of the second portion, from about 5 percent to about 80 percent, e.g. from about 5 percent to about 70 percent, of the first, semi-permeable coating layer; from about 10 percent to about 90 percent, e.g., from about 10 percent to about 80 percent of the second protective coating layer; and from about 1 percent to about 90 percent, e.g., from about 1 percent to about 80 percent of the active ingredient particle cores.

According to the present invention, the dosage form contains, based upon the total weight of the dosage form, from about 0.1 percent to about 90 percent, e.g., from about 1.0 percent to about 80 percent, of the first, immediate release active ingredient; and from about 0.005 percent to about 20 percent, e.g., from about 0.01 percent to about 10 percent of the second, modified release active ingredient.

The dosage forms of the present invention are intended to deliver an effective amount of a first active ingredient, such as an NSAID, which has an ATDAIRD of about 5, in the same dosage form as an effective amount of a second active ingredient, such as phenylephrine or psuedoephedrine, which as has an ATDAIRD of about 3 in one administration such that both active ingredients can be released from the dosage form throughout the longer ATDAIRD period.

In certain embodiments, the dosage form may be substantially coated with an optional subcoating layer, then substantially coated with an outer layer. In dosage forms having a subcoating, the dosage form may contain the subcoating in an amount, based upon the weight of the subcoated dosage form, from about 0.1 percent to about 10 percent, i.e., e.g., from about 0.5 percent to about 8 percent, or about 1 percent to about 7 percent. The use of subcoatings is well known in the art and disclosed in, for example, U.S. Pat. No. 3,185,626, which is incorporated by reference herein. Any composition suitable for film-coating a tablet may be used as a subcoating according to the present invention. Examples of suitable subcoatings are disclosed in U.S. Pat. Nos. 4,683,256, 4,543,370, 4,643,894, 4,828,841, 4,725,441, 4,802,924, 5,630,871, and 6,274,162, which are all incorporated by reference herein. Additional suitable subcoatings include one or more of the following ingredients: cellulose ethers such as hydroxypropylmethylcellulose, hydroxypropylcellulose, and hydroxyethylcellulose; polycarbohydrates such as xanthan gum, starch, and maltodextrin; plasticizers including for example, glycerin, polyethylene glycol, propylene glycol, dibutyl sebecate, triethyl citrate, vegetable oils such as castor oil, surfactants such as polysorbate-80, sodium lauryl sulfate and dioctyl-sodium sulfosuccinate; polycarbohydrates, pigments, and opacifiers.

In one embodiment, the subcoating may be comprised of, based upon the total weight of the subcoated dosage form, from about 2 percent to about 8 percent, e.g. from about 4 percent to about 6 percent of a water-soluble cellulose ether and from about 0.1 percent to about 1 percent castor oil, as disclosed in detail in U.S. Pat. No. 5,658,589, which is incorporated by reference herein. In another embodiment, the subcoating may be comprised of, based upon the total weight of the subcoating, from about 20 percent to about 50 percent, e.g., from about 25 percent to about 40 percent of HPMC; from about 45 percent to about 75 percent, e.g., from about 50 percent to about 70 percent of maltodextrin; and from about 1 percent to about 10 percent, e.g., from about 5 percent to about 10 percent of PEG 400.

The outer coating layer of the dosage form may be a release modifying coating or an immediate release coating. In dosage forms having an immediate release coating, the dosage form may contain the immediate release coating in an amount, based upon the weight of the final dosage form, from about 0.1 percent to about 20 percent, i.e., e.g., from about 0.5 percent to about 15 percent, or about 0.5 percent to about 5 percent. In dosage forms having an exterior release modifying coating, the dosage form may contain the release modifying coating in an amount, based upon the weight of the final dosage form, from about 5 percent to about 60 percent, i.e., e.g., from about 10 percent to about 50 percent, or about 15 percent to about 40 percent.

Examples of suitable release modifying coatings include film forming polymers such as, for example, any of the aforementioned water insoluble materials, pH dependent polymers, hydrophilic materials, and copolymers and mixtures thereof.

Examples of suitable immediate release coatings include, but are not limited to, coatings comprised of film forming water soluble polymers, suitable hydrocolloids, film forming proteins and copolymers and combinations thereof.

Suitable film-forming water soluble polymers include, but are not limited to, water soluble vinyl polymers such as polyvinylalcohol (PVA); water soluble polycarbohydrates such as hydroxypropyl starch, hydroxyethyl starch, pullulan, methylethyl starch, carboxymethyl starch, pre-gelatinized starches, and film-forming modified starches; water swellable cellulose derivatives such as hydroxypropyl cellulose (HPC), hydroxypropylmethyl cellulose (HPMC), methyl cellulose (MC), hydroxyethylmethylcellulose (HEMC), hydroxybutylmethylcellulose (HBMC), hydroxyethylethylcellulose (HEEC), and hydroxyethylhydroxypropylmethyl cellulose (HEMPMC); water soluble copolymers such as methacrylic acid and methacrylate ester copolymers, polyvinyl alcohol and polyethylene glycol copolymers, polyethylene oxide and polyvinylpyrrolidone, and copolymers; and derivatives and mixtures thereof.

Suitable film-forming proteins include those that may be natural or chemically modified, and include, but are not limited to gelatin, whey protein, myofibrillar proteins, coagulatable proteins such as albumin, casein, caseinates and casein isolates, soy protein and soy protein isolates, zein and polymers, derivatives and mixtures thereof.

Examples of suitable hydrocolloids include, but are not limited to, alginates, agar, guar gum, locust bean, carrageenan, tara, gum arabic, tragacanth, pectin, xanthan, gellan, maltodextrin, galactomannan, pusstulan, laminarin, scleroglucan, gum arabic, inulin, pectin, whelan, rhamsan, zooglan, methylan, chitin, cyclodextrin, chitosan. Examples of suitable gelling starches include acid hydrolyzed starches, and derivatives and mixtures thereof.

In one embodiment of the invention, the immediate release coating material is comprised of gelatin, which is a mixture of derived proteins of the albuminous class, which are ordinarily soluble in warm water. Two types of gelatin—Type A and Type B—are commonly used. Type A gelatin is a derivative of acid-treated raw materials. Type B gelatin is a derivative of alkali-treated raw materials. The moisture content of gelatin, as well as its Bloom strength, composition and original gelatin processing conditions, determine its transition temperature between liquid and solid. Bloom is a standard measure of the strength of a gelatin gel, and is roughly correlated with molecular weight. Bloom is defined as the weight in grams required to move a half-inch diameter plastic plunger 4 mm into a 6.67% gelatin gel that has been held at 10° C. for 17 hours. In a preferred embodiment, the flowable material is an aqueous solution comprising 20% 275 Bloom pork skin gelatin, 20% 250 Bloom Bone Gelatin, and approximately 60% water.

In one embodiment, a third coating layer may be added, wherein the resulting coated particles contain a first semipermeable coating, a second enteric coating and a third, outer pH independent elastic coating in order to prevent rupture of the first two coating layers during compression.

In another embodiment wherein the outer coating layer of the dual coated particle is enteric, the dosage form may be in the form of a suspension. In this embodiment, the suspension may comprise an uncoated NSAID in combination with the dual coated second active ingredient. The suspension vehicle may comprise carriers well-known in the art including, but not limited to glycerin, high fructose corn syrup, propylene glycol; structuring and suspending agents such as but not limited to hydrocolloids, xanthan gum, locust bean gum, carageenan, starch and modified starch; surfactants such as but not limited to polysorbate 80; sweeteners such as but not limited to sucralose, aspartame, acesulfame potassium, saccharin; flavors; acidulants, pH modifiers and preservatives such as but not limited to potassium sorbate and parabens.

In one embodiment, the dosage form is in the form of an aqueous pharmaceutical suspension composition and is comprised of, based upon the total weight of active ingredient per volume (w/v or g/100 ml) of the aqueous pharmaceutical suspension, from greater than about 0 percent to about 30 percent, e.g. about 0.05 percent to about 20 percent, or about 0.5 percent to about 10 percent, or about 0.5 percent to about 5 percent, of the first active ingredient and from greater than about 0 percent to about 10 percent, e.g. about 0.01 percent to about 10 percent, or about 0.03 percent to about 5 percent, of the second, modified release active ingredient.

In another embodiment wherein the first active ingredient is ibuprofen, the amount of first active ingredient in the immediate release portion of the suspension dosage form is, based upon the total weight of first active ingredient per volume (w/v) of the aqueous suspension dosage form, from about 25 mg to about 400 mg, i.e., e.g. from about 50 mg to about 200 mg, per teaspoonful of aqueous suspension dosage form. In one embodiment wherein the second active ingredient is phenylephrine or pseudoephedrine, the amount of second active ingredient in the modified release portion of the suspension dosage form is, based upon the total weight of second active ingredient per volume (w/v) of the aqueous suspension dosage form, from about 1 mg to about 20 mg, i.e., e.g. from about 1 mg to about 10 mg, per teaspoonful of aqueous suspension dosage form.

One embodiment of the present invention is directed to a liquid measurable suspension composition that includes, based upon the total weight of the suspension: a) from about 0.05 percent to about 40 percent of a first, immediate release active ingredient; b) from about 20 percent to about 80 percent of water; c) from about 0.1 percent to about 10 percent of a suspending system; d) from about 0 percent to about 40 percent, e.g. from about 20 percent to about 40 percent of a sweetening agent; e) from about 0 percent to about 0.5 percent of excipients; and from about 0.01 percent to about 10 percent of a second portion of modified release particles.

In one embodiment, the suspension dosage form contains an immediate release portion containing both ibuprofen and phenylephrine, and a modified release portion containing an additional amount of phenylephrine. In this embodiment, the immediate release dose of ibuprofen may range from about 25 mg/5 mL to about 200 mg/5 mL of suspension, i.e., e.g. about 50 mg/5 mL to about 200 mg/5 mL of suspension, and the immediate release dose of phenylephrine may range from about 2.5 mg to about 15 mg immediate release phenylephrine/5 mL suspension; i.e., e.g. about 2.5 mg to about 10 mg immediate release phenylephrine/5 mL suspension. In this embodiment, the modified release dose of phenylephrine may range from about 2.5 mg to about 20 mg modified release phenylephrine/5 ml of suspension; i.e., e.g. about 5 to about 15 mg modified release phenylephrine/5 mL suspension.

In certain embodiments the suspension dosage form may include any suspending systems known in the art, such as those that typically include one or more structuring agents and/or one or more swelling agents. In one embodiment, the dosage form contains, based upon the total weight of the liquid suspension dosage form, from about 0.1 percent to about 10 percent, of a suspending system. Suitable suspending systems include those disclosed in, for example, U.S. Pat. Nos. 5,374,659, 5,621,005, and 5,409,907, which are all incorporated by reference herein in their entireties.

Structuring agents that are suitable for use in the suspension dosage form include hydrophilic polymers such as hydrocolloids. Examples of suitable hydrocolloids include alginates, agar, guar gum, locust bean, carrageenan, tara, gum arabic, tragacanth, pectin, xanthan, gellan, maltodextrin, galactomannan, pusstulan, laminarin, scleroglucan, gum arabic, inulin, karaya, whelan, rhamsan, zooglan, methylan, chitin, cyclodextrin, chitosan, and combinations thereof. In certain embodiments of the present invention, xanthan gum is the structuring agent.

A swelling agent, when exposed to an appropriate aqueous environment, expands without forming a network system. Pregelatinized starch is a suitable swelling agent. Pregelatinized starch, also known as "instantized" starch, is precooked so that it swells and begins to thicken instantly when added to cold water. One particularly suitable pregelatinized starch is prepared from modified, stabilized and waxy, maize food starch, and is commercially available from National Starch Company as "INSTANT STARCH, ULTRASPERSE-M." Other suitable swelling agents include, but are not limited to microcrystalline cellulose and/or hydroxypropylmethylcellulose.

In one embodiment, the suspending system is comprised of a xanthan gum structuring agent with a pregelatinized starch swelling agent. In another embodiment, the suspending system is comprised of, based upon the total weight of the liquid suspension dosage form, from about 0.01 percent to about 1 percent or from about 0.05 percent to about 0.40 percent of xanthan gum and from about 1 percent to about 10 percent or from about 0.5 percent to about 3.0 percent of a pregelatinized starch such as that commercially available from National Starch Company under the tradename, "INSTANT STARCH, ULTRASPERSE-M."

In embodiments wherein the dosage form is in a liquid form, e.g., suspension or elixir, the pH of the liquid dosage form should be optimized to minimize the solubility and maximize the chemical stability of any uncoated active ingredient contained therein. In embodiments wherein the uncoated active agent is acidic, e.g., ibuprofen, the pH of the dosage form may be as close as possible to 2 pH units below the pKa of that acidic uncoated active agent. In certain embodiments employing ibuprofen as the uncoated active agent, the pH of the dosage form may be in the range from about 1.0 to about 5.0, e.g., from about 1.0 to about 4.0.

The suspension dosage form can be buffered using known pH adjusting agents to maintain the pH of the suspension in the desired pH range. Suitable pH-adjusting agents may be present in the dosage form in amounts sufficient to provide the desired degree of pH buffering. The pH-adjusting agents will typically be present in the range of from about 0 to about 1 gram per 100 mL of the dosage form.

In a supension embodiment containing ibuprofen as the uncoated active agent and a suspending system having alkaline polymers, such as for example sodium carboxymethylcellulose, the pH adjusting agent may be selected from weak organic acids, such as citric acid, malic acid, glutamic acid, and the like having acceptable taste characteristics for use in taste masked oral suspensions.

In one embodiment, the second outer coating layer or third outer coating layer possesses an elongation at break value of at least about 50%, when film samples of this layer are independently tested in accordance with that described in the American Society for Testing Materials (ASTM) D882 test measurement. According to this test method, a film sample is cast and cut or stamped using an ASTM D1708 Stamp mold, then inserted into a press such as the Punch Press Model B No. 8463 as produced by the Naef Corporation. The film sample is then placed between two grippers on a texture analyzer, such as the model TA-XT2i (HR) available from Texture Technologies Corporation, which elongates the film from two ends and determines the percentage value at break.

An "effective amount" of an analgesic is one that provides relief from pain in a patient. For example, a typical adult dose of ibuprofen may range from about 2.9 to about 12 mg/kg weight of the patient given every 4 to 6 hours, for a typical daily dose ranging from about 11.6 to about 72 mg/kg/day. Therefore, administration of an effective amount of ibuprofen to a typical 70 kg adult may involve once or twice daily administration of a tablet or multiple tablets containing about 200 mg to about 2400 mg of the formulation of the present invention, wherein a single tablet contains, for example, about 200 mg ibuprofen. A typical pediatric dose of ibuprofen may range from about 5 to about 10 mg/kg given every 4 to 6 hours, for a typical daily dose ranging from about 20 to about 60 mg/kg/day. Administration of an effective amount of ibuprofen to a typical 15 kg child may involve once or twice daily administration of a tablet or multiple tablets containing about 100 mg to about 600 mg of the formulation of the present invention wherein a single tablet contains, for example, about 100 mg ibuprofen.

An "effective amount" of a decongestant is one that provides effective relief of congestion, i.e. a medication that breaks up congestion, as that of the nasal passages and/or sinuses, by reducing swelling. For example, a typical adult dose of phenylephrine may range from about 0.14 to about 0.29 mg/kg weight of the patient given every 6 hours, or about 10 mg to about 20 mg given every 6 hours for a typical adult, with a typical daily dose ranging from about 0.60 to about 1.0 mg/kg/day, or about 0.86 mg/kg/day or about 60 mg phenylephrine per day for the typical adult. Therefore, administration of an effective amount of phenylephrine to a typical 70 kg adult may involve once to four times daily administration of a tablet or multiple tablets, wherein each tablet contains about 7.5 mg to about 30 mg, of a formulation of the present invention, and wherein a single tablet may contain, for example, about 15 mg phenylephrine. A typical pediatric dose of phenylephrine may range from about 0.25 to about 0.75 mg/kg given every 2 to 4 hours, or about 3.75 mg to about 11.25 mg given every 6 hours for a typical child, for a typical daily dose ranging from about 1.0 to about 2.7 mg/kg/day, or about 2 mg/kg/day, or about 30 mg of phenylephrine per day for the typical child. Administration of an effective amount of phenylephrine to a typical 15 kg child may involve once to four times daily administration of a tablet or multiple tablets, wherein each tablet contains about 3.75 mg to about 15 mg of the formulation of the present invention, and wherein a single tablet may contain, for example, about 3.75 mg phenylephrine.

In one embodiment, the oral administration of the dosage forms of the present invention provides the user with the first active ingredient, such as NSAIDs, in a modified release dose that continues to release the second active ingredient from the dosage form so that the duration of its therapeutic effect is comparable to that of the first active ingredient.

In one embodiment, the solid or semi-solid dosage form contains an immediate release portion containing both ibuprofen and phenylephrine, and a modified release portion containing an additional amount of phenylephrine. In this embodiment, the dosage form may contain, based upon the total weight of the dosage form, from about 25 mg to about 400 mg, i.e., e.g. from about 50 mg to about 200 mg of an immediate release dose of ibuprofen, and from about 2.5 mg to about 15 mg, i.e., e.g., from about 5 mg to about 10 mg of an immediate release dose of phenylephrine, and from about 2.5 mg to about 20 mg, i.e., e.g., about 5 mg to about 15 mg of a modified release dose of phenylephrine.

Another embodiment of the present invention is directed to method for alleviating nasal and respiratory congestion in persons in need thereof with the oral administration of pseudoephedrine or phenylepherine, as well as ameliorating associated conditions such as headache, joint pain, watery nasal passages, weeping eyes, sinus congestion and pain, coughing, excessive exudating of mucus, and bronchitis by way of administering the subject dosage forms of the present invention to such persons.

In one particular embodiment the dosage form contains an immediate release dose of ibuprofen, an immediate release dose of cetirizine and a modified release portion of a decongestant such as phenylephrine or pseudoephedrine. In this embodiment, the dose of cetirizine can range from about 5 mg to about 10 mg in a dosage form.

In one embodiment, the active ingredients may be delivered in a liquid or semi-solid filled dosage form, such as a capsule. In this embodiment, the coated modified release active ingredient particles comprise, based upon the total weight of the capsule fill, from about 0.1 percent to about 20, i.e., e.g. about 0.1 percent to about 10 percent, and the immediate release active ingredient comprises, based upon the total weight of the capsule fill, from about 1 percent to about 60 percent, i.e., e.g. from about 5 percent to about 50 percent. The capsule fill materials may be comprised of, based upon the total weight of the fill, from about 20 percent to about 80 percent, i.e., e.g. about 30 percent to about 70 percent. In this embodiment, suitable capsule filling materials may be used including but not limited to alkalizing agents, suitable solvents and solubilizers, and mixtures thereof.

Examples of suitable solvents and solubilizers suitable for use as fill excipients include, but are not limited to, vegetable oils; neutral oils and triglycerides; polyethylene glycol; polyoxyethylene stearates; purified lecithin; glycerol esters of fatty acids; lecithin combined in propylene glycol; caprylcaproyl macrogol-8-glyceride; caproyl caproyl macrogol-8 glycerides; polyethoxylated hydrogenated castor oil; and mixtures thereof.

Example of suitable solvents and solubilizers include the chemical class of vegetable oils including but not limited to vegetable oil triglycerides and triacylglycerols, and specifically, for example, corn oil.

Suitable solvents and solubilizers also include the chemical class of polyglycolized glycerides, which includes but is not limited to, lauryl macrogol 32-glycerides and steroyl macrogol 32-glycerides, such as those sold under the tradename, "Gelucire® 44/14" and "Gelucire® 50/13," available from the Gattefosse Corporation, as well as the chemical class of glycerol esters of fatty acids such as those sold under the tradename "Gelucire® 33/01," "Gelucire® 39/01," and "Gelucire® 43/01" available from the Gattefosse Corporation, and mixtures thereof.

Suitable solvents and solubilizers further include the chemical class of neutral oils and triglycerides including but not limited to, medium chain triglycerides, fractionated coconut oil, caprylic and capric triglycerides such as those sold under the tradename, "Miglyol® 812" available from the Condea Vista Corporation, and mixtures thereof.

Suitable solvents and solubilizers further include the chemical class of polyethylene glycol and polyoxyethylene stearates, which includes but is not limited to polyethylene glycol 15 hydroxystearate as sold under the tradename, "Solutol® HS 15" available from the BASF Corporation, and mixtures thereof.

Suitable solvents and solubilizers also include the chemical class of purified vegetable, soybean and egg yolk lecithin, which includes but is not limited to, phosphatidyl choline, 1,2-diacyl-sn-glycero-3-phosphoryl choline such as those sold under the tradename, "Phospholipon® 90 G" available from the American Lecithin Company, and mixtures thereof. Suitable solvents and solubilizers also include the chemical class of lecithin combined in propylene glycol, which includes but is not limited to standardized mixtures of phosphatidylcholine, propylene glycol, mono- and di-glycerides, ethanol, soya fatty acids and ascorbyl palmitate, such as those sold under the tradename, "Phosal® 50 PG," available from the American Lechitin Coporation.

Suitable solvents and solubilizers also include the chemical class of capryl-caproyl macrogol-8-glyceride and caproyl caproyl macrogol-8 glycerides, such as those sold under the tradename, "Labrasol®" available from the Gattefosse Corporation, and mixtures thereof.

Suitable solvents and solubilizers also include the chemical class of polyethoxylated hydrogenated castor oil, which includes but is not limited to, glycerol-polyethylene glycol oxystearate, such as those sold under the tradename Cremophor® RH 40 available from the BASF Corporation, and mixtures thereof.

Suitable alkalizing agents include, but are not limited to, sodium bicarbonate, potassium bicarbonate, potassium hydroxide, sodium hydroxide, and mixtures thereof.

In one particular liquid or semi-solid filled capsule embodiment, the ibuprofen may be present in a solubilized state (i.e., e.g., dissolved in the capsule fill materials) and the modified release particles containing decongestant may be present in a dispersed state (i.e., e.g., suspended in the capsule fill materials).

Beneficially, we have unexpectedly found how to effectively stabilize the release characteristics of the modified release portion of a solid or semi-solid dosage form throughout the shelf life of the product and throughout the period of treatment. Specifically, we have overcome the challenge of preventing active ingredient release from the particles in the product prior to ingestion, while enabling modified release of active ingredient from those same particles in the gastro-intestinal fluids.

We further have found how to extend the duration of the therapeutic effect of the second, coated active agent to a duration comparable to that possessed by the uncoated, first active agent by overcoming the interaction between the first active agent and the semi-permeable coating on the second agent.

Advantageously, the formulations of the present invention may be used in a variety of formats including, for example, (i) accurately-measurable single dose dry formulations; (ii) multi-dose granular formulations having significant dose flexibility obtainable by measuring different amount of granules to be resuspended on an as-needed basis; (iii) liquid filled capsules; (iv) powder or granular filled capsules; (v) chewy solid forms, (vi) semi-solid filled liquid capsules (vii) coated tablets (viii) simulated capsule like medicaments and (vix) suspensions or elixirs.

In addition, since the formulation is convenient to administer and swallow, and the number of daily doses of active ingredient is reduced, the overall patient compliance is achieved. Additional benefits are anticipated in pediatric practice due to the ease of swallowing and administering.

The following examples further illustrate the invention, but are not meant to limit the invention in any way.

EXAMPLE 1

Preparation of Phenylephrine Layered Particle Core

Part A: Preparation of Phenylephrine Layering Solution:
A layering solution is prepared by dissolving 1440.0 grams of phenylephrine hydrochloride into a 5 Liter stainless steel vessel containing 1600 g of purified water with mixing using a laboratory mixer at 50 RPM for at least 30 minutes.

Part B: Preparation of Phenylephrine Particle Core:
5760 g of a modified starch commercially available from Grain Processing Corporation under the tradename, "Instant Pure-Cote®," and 800 g of Carnuba Wax are placed into a Glatt fluid bed GPCG-5/9 fluid bed processing unit. After spraying the layering solution from Step A onto the starch substrate for approximately 40 minutes at an inlet temperature of about 47° C. and a spray rate of about 55 g/minute, the resulting particle cores are dried to 28° C. The resulting dry particle cores contain approximately 18.0% phenylephrine and have a mean particle size of approximately 300 microns.

EXAMPLE 2

Preparation of Ethylcellulose Semipermeable First Coating Solution

A coating solution is prepared by dissolving 350 grams of ethylcellulose, which is commercially available from Dow Chemical Corporation under the tradename, "Ethocel 10 CPS," and 87.5 g of dibutyl sebecate (DBS), in a solvent containing, based upon the total weight of the solvent, 1531.25 g of acetone and 1531.25 g of isopropyl alcohol (a 50:50 mixture) under ambient conditions with mixing using a laboratory mixer at 75 RPM for at least 60 minutes.

The resulting coating solution contains, based upon the total wet coating solution, about 10% of ethylcellulose, about 2.5% DBS, about 43.75% acetone, and about 43.75% isopropyl alcohol. The resulting coating solution contain about 12.5% solids comprised of, based upon the total weight percent of the dried coating solution, about 80 percent ethylcellulose and about 20 percent DBS.

EXAMPLE 3

Preparation of pH Independent Protective Second Coating Solution

A protective coating solution is prepared by dispersing 1000.0 g of ethylacrylate methylmethacrylate copolymers dispersion (30% solids), which is commercially available from Rohm Pharma under the tradename, "Eudragit NE-30D," in 745.0 g of purified water with mixing at 25 RPM under ambient conditions for 5 minutes. 3.1 g of a simethicone emulsion, which is a water dilutable nonionic emulsion commercially available from the Dow Corporation as "Q7-2587" and which contains 30% simethicone)., 2.6 g of polysorbate-80, and 60.0 g of calcium stearate are then added sequentially thereto with mixing at 50 RPM for at least 30 minutes.

The resulting protective coating solution contains, based upon the total wet coating solution, about 55 percent of Eudragit NE-30D (30% of which are as solids), about 0.17 percent of the simethicone emulsion, about 0.14 percent of polysorbate-80, about 3 percent of calcium stearate and about 41 percent of purified water.

The relative amounts of solids are, based upon the total weight percent of the dried protective coating solution, about 82 percent of Eudragit NE-30D, about 0.9 percent of the simethicone emulsion, about 0.7 percent of polysorbate-80 and about 16.4 percent of calcium stearate.

EXAMPLE 4

Preparation of Phenylephrine Coated Particles with a Single, Semipermeable Ethylcellulose Layer 1000.0 grams of the phenylepherine particle cores from Example 1 are placed into a Glatt GPCG-⅓ coating unit then coated with the ethylcellulose semipermeable coating solution prepared in accordance with Example 2 by spraying the solution at a rate of about 16.0 g/min under product temperature conditions of about 38-40° C., with an atomization air pressure of approximately 2 bar. The resulting coated phenylephrine granules contain, based upon the total dry weight of the coated phenylephrine granules, about 30% of the semipermeable coating. The resulting coated particles have a mean particle size of approximately 430 microns.

EXAMPLE 5

Preparation of Coated Phenylephrine Particles Coated with an Semipermeable Layer and a pH Independent Outer Protective Layer 1000.0 grams of the coated phenylephrine particles prepared in accordance with Example 4 are placed into a Glatt GPCG-⅓ coating unit and coated with the Eudragit NE-30D protective coating solution prepared in accordance with Example 3 by spraying the solution at a rate of about 9.0 g/min under product temperature conditions of about 23-24° C., and with an atomization air pressure of approximately 2 bar. The resulting coated phenylephrine granules contain, based upon the total dry weight of the double-coated phenylephrine granules, about 27 percent of the outer, protective coating. The amount of ingredients in the final dried, double-coated particles are shown in Table 1 below:

TABLE 1

Dried Coated Particle Formulation

| Ingredients | Tradename | Percent % (w/w) |
|---|---|---|
| Phenylephrine HCl | | 9.2 |
| Instant Starch | Pure-cote | 36.6 |
| Carnuba Wax | | 5.1 |
| Ethylcellulose 10 CPS | Ethocel | 17.8 |
| Dibutyl Sebecate | | 4.3 |
| Ethylacrylate methylmethacrylate | Eudragit NE-30D | 22.0 |
| Simethicone Emulsion | | 0.2 |
| Polysorbate-80 | Tween-80 | 0.2 |
| Calcium Stearate | | 4.4 |
| TOTAL | | 100.0 |

EXAMPLE 6

Production of the Tablet Base Blend & Compressed Tablets Containing Immediate Release Ibuprofen and Coated Phenylephrine All materials set forth in Table 2 below (except for the coated phenyelphrine and the ibuprofen) are manually passed through a 30 mesh screen. The screened materials, coated phenylephrine and ibuprofen are then placed into a 4 quart V-Blender, mixed for 5 minutes, then discharged to give the final blend as set forth in Table 2:

TABLE 2

Components of Tablet Base Blend

| Ingredients | Percent (w/w) | mg/tab |
|---|---|---|
| Coated Phenylephrine (9.2% active)* | 32.94 | 217.39 |
| Ibuprofen USP 115 μm Grade | 30.30 | 200.00 |
| Crospovidone | 0.75 | 4.95 |
| Microcrystalline Cellulose (Avicel PH | 5.00 | 33.00 |
| Lactose | 30.26 | 199.72 |
| Magnesium Stearate | 0.75 | 4.95 |
| TOTAL | 100.0 | 660.0 |

*Equivalent to a 20 mg Dose of Phenylephrine; Coated phenylephrine particles are produced in accordance with Example 5.

The resulting blend is then removed from the blender and compressed on a rotary tablet press at 60 rpm using 7/16 inch extra deep concave tablet tooling in order to yield tablets having a weight of about 660 mg and a hardness range of about 3 to about 7 kiloponds as determined by the Hardness test set forth in Lieberman, and a thickness of about 0.300 to about 0.310 inches.

EXAMPLE 7

Preparation of an Enteric Outer Protective Layer Solution (for use as Second Layer Protective Coating)

A coating solution is prepared by dispersing 1947.3 g of methacrylate copolymer dispersion (30% solids), which is commercially available under the tradename, "Eudragit L30D-55," from Rohm Pharma, in 1112.7 g of purified water with mixing at 25 RPM under ambient conditions for 5 minutes. 23.5 g of glycerol monostearate and 58.9 g of triethylcitrate is then added thereto with mixing at 50 RPM for at least 30 minutes.

The resulting coating solution contained, based upon the total wet coating solution, about 62 percent of Eudragit L30D-55 (30% of which are as solids), about 0.8 percent glycerol monostearate, about 0.9 percent of triethylcitrate and about 35.4 percent of purified water.

The relative amounts of solids in the coating solution is, based upon the total weight percent of the dried coating solution, about 88 percent Eudragit L30D-55, 4 percent of glycerol monostearate, and 1.9 percent of triethylcitrate.

EXAMPLE 8

Preparation of Coated Phenylephrine Particles Coated with an Semipermeable Layer and an Outer Enteric Protective Layer 1000.0 grams of the coated phenylephrine particles prepared in accordance with Example 4 are placed into a Glatt GPCG-⅓ coating unit and coated with the Eudragit L-30D-55 protective coating solution prepared in accordance with Example 7 by spraying the solution at a rate of about 15.0 g/min under product temperature conditions of about 54° C. to about 71+ C., and with an atomization air pressure of approximately 2 bar. The resulting coated phenylephrine granules contain, based upon the total dry weight of the double-coated phenylephrine granules, about 40 percent of the outer, protective enteric coating.

The amount of ingredients in the final dried, double-coated particles are shown in Table 3.

TABLE 3

Dried Coated Particle Formulation

| Ingredients | Tradename | Percent % (w/w) |
|---|---|---|
| Phenylephrine HCl | | 7.5 |
| Instant Starch | Pure-cote | 30.1 |
| Carnuba Wax | | 4.2 |
| Ethylcellulose 10 CPS | Ethocel | 14.6 |
| Dibutyl Sebecate | | 3.6 |
| Methacrylate Co-Polymer (Enteric | Eudragit L30D55 | 35.1 |
| Glycerol Monostearate | | 1.4 |
| Triethyl Citrate | | 3.5 |
| TOTAL | | 100.0 |

EXAMPLE 9

Production of the Tablet Base Blend & Compressed Tablets Containing Immediate Release Ibuprofen and Coated Phenylephrine (with Enteric Outer Layer Coating)

All materials set forth in Table 4 below (except the encapsulated phenylepherine and the ibuprofen) are manually passed through a 30 mesh screen. The screened materials, coated phenylephrine and ibuprofen are then placed into a 4 quart V-Blender and mixed for 5 minutes and discharged to give the final blend as set forth in Table 4 below:

TABLE 4

Components of Tablet Base Blend

| Ingredients | Percent (w/w) | mg/tab |
|---|---|---|
| Coated Phenylephrine (7.5% active)* | 40.40 | 266.67 |
| Ibuprofen USP 115 μm Grade | 30.30 | 200.00 |
| Crospovidone | 0.75 | 4.95 |
| Microcrystalline Cellulose (Avicel PH) | 5.00 | 33.00 |
| Lactose | 22.79 | 150.43 |
| Magnesium Stearate | 0.75 | 4.95 |
| TOTAL | 100.0 | 660.0 |

*Equivalent to a 20 mg Dose of Phenylephrine. Coated phenylephrine particles produced in accordance with Example 8.

The resulting blend is compressed on a rotary tablet press at 60 rpm using 7/16 inch extra deep concave tablet tooling in order to yield tablets having a weight of 660 mg and a hardness range of about 3 to about 7 kiloponds as determined by the Hardness test set forth in Lieberman, and a thickness of about 0.300 to about 0.310 inches.

EXAMPLE 10

Preparation of Coated Phenylephrine Particles Coated with a Semipermeable Layer, a Second Enteric Layer and an Outer Elastic Protective Layer 1000.0 g of coated phenylephrine prepared according to Example 8 are coated with the protective pH independent layer prepared in accordance with Example 3, to yield coated particles with 3 layers: an ethylcellulose semipermeable internal layer, an Eudragit L-30D enteric intermediate layer, and an Eudragit NE30D elastic pH independent exterior layer as follows:

The coated phenylephrine of Example 3 is placed into a Glatt GPCG-⅓ coating unit and coated with the Eudragit NE30D elastic pH Independent layer by spraying the solution at a rate of about 9.0 g/min under product temperature conditions of about 23-24° C. and an atomization air pressure of approximately 2 bar. The resulting coated phenylephrine granules contain, based upon the total weight of the coated granules, about 27 percent of the outer, protective pH independent coating. The amount of ingredients in the final dried, triple-coated particles are shown in Table 5 below.

TABLE 5

Dried Coated Particle Formulation

| Ingredients | Tradename | Percent % (w/w) |
|---|---|---|
| Phenylephrine HCl | | 5.5 |
| Instant Starch | Pure-cote | 22.0 |
| Carnuba Wax | | 3.1 |
| Ethylcellulose 10 CPS | Ethocel | 10.7 |
| Dibutyl Sebecate | | 2.6 |
| Methacrylate Co-Polymer (Enteric polymer) | Eudragit L30D55 | 25.7 |
| Glycerol Monostearate | | 1.0 |
| Triethyl Citrate | | 2.6 |
| Ethylacrylate methylmethacrylate | Eudragit NE-30D | 22.0 |

TABLE 5-continued

Dried Coated Particle Formulation

| Ingredients | Tradename | Percent % (w/w) |
|---|---|---|
| Simethicone Emulsion | | 0.2 |
| Polysorbate-80 | Tween-80 | 0.2 |
| Calcium Stearate | | 4.4 |
| TOTAL | | 100.0 |

EXAMPLE 11

Preparation of Tablet Base Blend and Compressed Tablets Containing Immediate Release Ibuprofen and Triple Coated Phenylephrine All materials set forth in Table 6 below (except the encapsulated phenylepherine and the ibuprofen) are manually passed through a 30 mesh screen. The screened materials, coated phenylephrine and ibuprofen are then placed into a 4 quart V-Blender and mixed for 5 minutes and discharged to give the final blend.

TABLE 6

Components of Tablet Base Blend

| Ingredients | Percent (w/w) | mg/tab |
|---|---|---|
| Coated Phenylephrine (5.5% active)* | 55.10 | 363.63 |
| Ibuprofen USP 115 μm Grade | 30.30 | 200.00 |
| Crospovidone | 0.75 | 4.95 |
| Microcrystalline Cellulose (Avicel PH) | 5.00 | 33.00 |
| Lactose | 8.10 | 53.47 |
| Magnesium Stearate | 0.75 | 4.95 |
| TOTAL | 100.0 | 660.0 |

*Equivalent to a 20 mg Dose of Phenylephrine. Coated phenylephrine particles produced in accordance with Example 10.

The resulting blend is compressed on a rotary tablet press at 60 rpm using 7/16 inch extra deep concave tablet tooling in order to yield tablets having a weight of 660 mg and a hardness range of about 3 to about 7 kiloponds as determined by the Hardness test set forth in Lieberman, and a thickness of about 0.300 to about 0.310 inches.

EXAMPLE 12

Preparation of a Reverse-Enteric Protective Coating Solution

A coating solution is prepared by dissolving 600 g of poly (butyl methacrylate, (2-dimethylaminoethyl)methacrylate, methyl methacrylate) 1:2:1, which is commercially available under the tradename, "Eudragit E100," from Rohm Pharma, in 6000 g of acetone with mixing at 25 RPM under ambient conditions for 5 minutes. 66.67 g of triethylcitrate is then added thereto with mixing at 50 RPM for at least 30 minutes.

The resulting coating solution contains, based upon the total wet coating solution, about 9 percent of Eudragit E100, about 1 percent triethylcitrate, and about 90 percent of acetone.

EXAMPLE 13

Preparation of Coated Phenylephrine Particles Coated with an Semipermeable Layer and an Outer Reverse-Enteric Protective Layer 1000.0 grams of the coated phenylephrine particles prepared in accordance with Example 4 are placed into a Glatt GPCG-⅓ coating unit and coated with the Eudragit E-100 protective coating solution prepared in accordance with Example 12 by spraying the solution at a rate of about 20 g/min under product temperature conditions of about 28° C. to about 35° C., and with an atomization air pressure of approximately 2 bar. The resulting coated phenylephrine granules contain, based upon the total dry weight of the double-coated phenylephrine granules, about 40 percent of the outer, protective reverse-enteric coating.

The amount of ingredients in the final dried, double-coated particles are shown in Table 7.

TABLE 7

Dried Coated Particle Formulation

| Ingredients | Tradename | Percent % (w/w) |
|---|---|---|
| Phenylephrine HCl | | 7.5 |
| Instant Starch | Pure-cote | 30.1 |
| Carnuba Wax | | 4.2 |
| Ethylcellulose 10 CPS | Ethocel | 14.6 |
| Dibutyl Sebecate | | 3.6 |
| Methacrylate Co-Polymer (Reverse-Enteric) | Eudragit | 36.0 |
| Triethyl Citrate | | 4.0 |
| TOTAL | | 100.0 |

EXAMPLE 14

Preparation of a Semi-Solid Filled Capsule Containing Solubilized Ibuprofen and Coated Phenylephrine A total of 200 g of fill material blend is prepared by heating the polyethylene glycol 400 and polyethylene glycol 3350 in amounts shown in Table 8 to 60° C. in a suitable stainless steel beaker with manualmixing until a clear solution is obtained. The potassium hydroxide and ibuprofen are then added thereto with mixing until dissolved. The coated phenylephrine is then added thereto with manual mixing, and the resulting blend is filled into interlocking hard gelatin capsule shells and sealed.

TABLE 8

Components of Semi-Solid Capsule Blend Fill

| Ingredients | Percent (w/w) | mg/capsule |
|---|---|---|
| Coated Phenylephrine (7.5% active)* | 29.63 | 266.67 |
| Ibuprofen USP 70 μm Grade | 22.22 | 200.00 |
| Polyethylene Glycol 3350 | 41.67 | 375.00 |
| Polyethylene Glycol 400 | 4.81 | 43.33 |
| Powdered Potassium Hydroxide | 1.88 | 15.00 |
| TOTAL | 100.0 | 900.0 |

*Coated Phenylephrine Prepared in accordance with Example 13 and is equivalent to 20 mg phenylephrine hydrochloride

EXAMPLE 15

Preparation of a Semi-Solid Filled Capsule Containing Suspended Ibuprofen and Coated Phenylephrine A total of 200 g of fill material blend is prepared by manually mixing high fructose corn syrup in the amount shown in Table 9 in a suitable stainless steel beaker, then adding the ibuprofen and the coated phenylephrine are then added thereto with a manual mixing. The resulting blend is filled into interlocking hard gelatin capsule shells and sealed.

TABLE 9

Components of Semi-Solid Capsule Blend Fill

| Ingredients | Percent (w/w) | mg/capsule |
|---|---|---|
| Coated Phenylephrine (7.5% active)* | 29.63 | 266.67 |
| Ibuprofen USP 70 μm Grade | 22.22 | 200.00 |
| High Fructose Corn Syrup | 48.14 | 433.3 |
| TOTAL | 100.0 | 900.0 |

*Coated Phenylephrine Prepared in accordance with Example 8 and is equivalent to 20 mg phenylephrine hydrochloride

We claim:

1. A solid or semi-solid pharmaceutical dosage form comprising:
   a) a first portion comprising ibuprofen and/or a pharmaceutically acceptable salt thereof, wherein the first active ingredient is released from the dosage form in a immediate release manner upon contact of the dosage form with a dissolution medium; and
   b) a second portion comprising:
   i. particle cores comprised of a second active ingredient, wherein said second active ingredient is phenylephrine or a pharmaceutically acceptable salt thereof;
   ii. a semi-permeable coating layer covering said particle cores to form coated particles, wherein said semi-permeable coating layer comprises ethylcellulose; and
   iii. a protective coating layer covering said coated particles, wherein the second active ingredient is released from the second portion in a modified release manner upon contact of the dosage form with the dissolution medium, and
   wherein the duration of the therapeutic effect of the second active ingredient and the duration of the therapeutic effect of the first active ingredient is about 4 hours to about 6 hours.

2. The dosage form of claim 1 further comprising a matrix.

3. The dosage form of claim 1, wherein said semi-permeable coating layer further comprises one or more agents selected from the group consisting of cellulose acetate, non-enteric polymethacrylates, and mixtures thereof.

4. The dosage form of claim 1, wherein said protective coating layer comprises enteric polymers selected from the group consisting of hydroxypropyl methylcellulose phthalate, hydroxypropyl methylcellulose acetate succinate, cellulose acetate phthalate, polyvinylacetate phthalate, shellac, enteric polymethacrylate-based polymers, and copolymers and mixtures thereof.

5. The dosage form of claim 1, wherein the protective coating layer-comprises a lipid, a wax, or mixtures thereof.

6. The dosage form of claim 1, wherein the protective coating layer-comprises an enteric coating, and wherein the particle cores of the second portion comprise a third pH independent protective coating layer that covers the protective coating layer.

7. The dosage form of claim 1, wherein said protective coating layer comprises a material selected from the group consisting of sucrose fatty acid esters; monoglycerides; diglycerides; triglycerides; glyceryl behenate; glyceryl palmitostearate; glyceryl tristearate; glyceryl trilaurylate; glyceryl myristate; lauroyl macrogol-32 glycerides; stearoyl macrogol-32 glyceride; fatty acid esters having a fatty acid chain length of about C10 to about C40; and mixtures thereof.

8. The dosage form of claim 1, wherein said protective coating layer comprises a wax selected from the group consisting of carnauba wax, spermaceti wax, beeswax, candelilla wax, shellac wax, beeswax, microcrystalline wax, and paraffin wax, and mixtures thereof.

9. The dosage form of claim 1, wherein the semi-permeable coating layer further comprises, based upon the total dry weight of the semi-permeable coating layer, from about 0.1% to about 40% of a plasticizer.

10. The dosage form of claim 1, wherein the protective coating further comprises, based upon the total dry weight of the protective coating, from about 0.1% to about 40% of a plasticizer.

11. The dosage form of claim 1, wherein the weight ratio of the semipermeable coating layer to the protective coating layer is about 10:90 to about 90:10.

12. The dosage form of claim 1, wherein the second portion comprises of, based upon the total dry weight of the second portion,
   a) from about 5 percent to about 80 percent of the semi-permeable coating layer;
   b) from about 10 percent to about 90 percent of the protective coating layer; and
   c) from about 20 percent to about 80 percent of the particle cores.

13. The dosage form of claim 1, wherein the dosage form comprises, based upon the total weight of the dosage form, from about 1.0% to about 80% of the first portion; and from about 0.01% to about 15% of the second portion.

14. The dosage form of claim 1, wherein the dosage form comprises, based upon the total weight of the dosage form,
   a) from about 1.0% to about 80% of the first active ingredient; and
   b) from about 0.01% to about 10% of the second active ingredient.

15. The dosage form of claim 1, wherein the dosage form is coated with an outer coating comprised of a release modifying coating or an immediate release coating.

16. The dosage form of claim 15, further comprising a subcoating intermediate to the outer coating.

17. The dosage form of claim 1, wherein the protective layer comprises a material selected from the group consisting of enteric polymers, lipids, waxes, elastic coatings, and copolymers and mixtures thereof.

* * * * *